(12) United States Patent
Wikswo et al.

(10) Patent No.: US 7,977,089 B2
(45) Date of Patent: *Jul. 12, 2011

(54) BIOREACTORS WITH MULTIPLE CHAMBERS

(75) Inventors: John P. Wikswo, Brentwood, TN (US);
Franz J. Baudenbacher, Franklin, TN (US); David Cliffel, Nashville, TN (US);
Frederick R. Haselton, Nashville, TN (US); Eugene J. Leboeuf, Franklin, TN (US); Ales Prokop, Franklin, TN (US);
Randall S. Reiserer, Nashville, TN (US); Mark A. Stremler, Franklin, TN (US)

(73) Assignee: Vanderbilt University, Nashville, TN (US)

( * ) Notice: Subject to any disclaimer, the term of this patent is extended or adjusted under 35 U.S.C. 154(b) by 1350 days.

This patent is subject to a terminal disclaimer.

(21) Appl. No.: 10/525,549

(22) PCT Filed: Aug. 27, 2003

(86) PCT No.: PCT/US03/26798
§ 371 (c)(1),
(2), (4) Date: Oct. 24, 2005

(87) PCT Pub. No.: WO2004/020590
PCT Pub. Date: Mar. 11, 2004

(65) Prior Publication Data
US 2006/0166354 A1   Jul. 27, 2006

Related U.S. Application Data

(60) Provisional application No. 60/406,278, filed on Aug. 27, 2002.

(51) Int. Cl.
*C12M 1/22* (2006.01)
*C12M 3/00* (2006.01)
*C12M 1/34* (2006.01)

(52) U.S. Cl. .......... 435/305.2; 435/288.7; 435/808; 435/288.4; 435/288.5; 435/297.1; 435/305.1; 435/297.5; 205/777.5; 205/778; 205/779; 204/403.01

(58) Field of Classification Search ............... 435/288.7, 435/808, 288.4, 288.5, 297.1, 297.5, 305.1, 435/305.2; 205/777.5, 778, 779; 204/403.01
See application file for complete search history.

(56) References Cited

U.S. PATENT DOCUMENTS
2,157,438 A   5/1939   Sparks
(Continued)

FOREIGN PATENT DOCUMENTS
WO   WO 01/07892 A1   2/2001
(Continued)

OTHER PUBLICATIONS

Harvath, L. et al, "Rapid quantitation of neutrophil chemotaxis; use of a polyvinylpyrrolidone-free polycarbonate membrane in multiwell assembly," *J. Immunol Method*, vol. 37, No. 1, 1980, pp. 39-45.
(Continued)

*Primary Examiner* — Nathan A Bowers
(74) *Attorney, Agent, or Firm* — Morris Manning & Martin LLP; Tim Tingkang Xia, Esq.

(57) ABSTRACT

A bioreactor for cultivating living cells in a liquid medium. In one embodiment of the present invention, the bioreactor has a first substrate having a first surface and an opposite second surface, defining a chamber therebetween for receiving the cells and the liquid medium. The bioreactor further has a barrier dividing the chamber into a first subchamber and a second subchamber, wherein the barrier has a porosity to allow the first subchamber and the second subchamber in fluid communication and allow at least one predetermined type of cells to permeate between the first subchamber and the second subchamber.

27 Claims, 3 Drawing Sheets

U.S. PATENT DOCUMENTS

| | | | |
|---|---|---|---|
| 4,201,845 A | 5/1980 | Feder et al. | |
| 4,391,151 A | 7/1983 | Nelson et al. | |
| 4,988,623 A | 1/1991 | Schwarz et al. | |
| 5,068,195 A | 11/1991 | Howell et al. | |
| 5,089,385 A | 2/1992 | Kiel et al. | |
| 5,139,946 A | 8/1992 | Howell et al. | |
| 5,376,548 A | 12/1994 | Matsuo et al. | |
| 5,443,985 A | 8/1995 | Lu et al. | |
| 5,489,515 A | 2/1996 | Hatschek et al. | |
| 5,520,787 A * | 5/1996 | Hanagan et al. | 204/403.14 |
| 5,589,352 A * | 12/1996 | Breznak et al. | 435/34 |
| 5,624,537 A | 4/1997 | Turner et al. | |
| 5,635,358 A | 6/1997 | Wilding et al. | |
| 5,955,029 A | 9/1999 | Wilding et al. | |
| 6,124,138 A | 9/2000 | Woudenberg et al. | |
| 6,168,948 B1 | 1/2001 | Anderson et al. | |
| 6,171,239 B1 | 1/2001 | Humphrey | |
| 6,197,575 B1 | 3/2001 | Griffith et al. | |
| 6,221,659 B1 | 4/2001 | Soule et al. | |
| 6,267,858 B1 | 7/2001 | Parce et al. | |
| 6,391,558 B1 | 5/2002 | Henkens et al. | |
| 6,440,645 B1 | 8/2002 | Yon-Hin et al. | |
| 6,506,345 B1 | 1/2003 | Lee et al. | |
| 6,642,019 B1 | 11/2003 | Anderson et al. | |
| 6,660,517 B1 | 12/2003 | Wilding et al. | |
| 6,673,594 B1 | 1/2004 | Owen et al. | |
| 6,855,542 B2 | 2/2005 | DiMilla et al. | |
| 6,890,762 B1 * | 5/2005 | Sugihara et al. | 436/503 |
| 7,238,323 B2 | 7/2007 | Knapp et al. | |
| 7,790,443 B2 | 9/2010 | Wikswo et al. | |
| 2001/0044143 A1 | 11/2001 | Herman et al. | |
| 2002/0025547 A1 | 2/2002 | Rao | |
| 2002/0055166 A1 | 5/2002 | Cannon et al. | |
| 2002/0058329 A1 | 5/2002 | Singh et al. | |
| 2002/0086280 A1 * | 7/2002 | Lynes et al. | 435/4 |
| 2002/0106786 A1 | 8/2002 | Carcalho et al. | |
| 2002/0164816 A1 | 11/2002 | Quake | |
| 2003/0003571 A1 * | 1/2003 | Kanegasaki et al. | 435/288.5 |
| 2003/0107946 A1 | 6/2003 | Cosby et al. | |
| 2004/0045891 A1 | 3/2004 | Gilbert et al. | |
| 2004/0142409 A1 * | 7/2004 | Allen et al. | 435/29 |
| 2005/0032204 A1 * | 2/2005 | Rodgers et al. | 435/288.5 |
| 2006/0166354 A1 | 7/2006 | Wikswo et al. | |
| 2006/0194273 A1 * | 8/2006 | Thomas | 435/29 |

FOREIGN PATENT DOCUMENTS

| | | |
|---|---|---|
| WO | 02/46355 A1 | 6/2002 |

OTHER PUBLICATIONS

Jain et al., "*In Vitro and In Vivo Quantificatiaon of Adhesion Between Leukocytes and Vascular Endothelium*," Tissue engineering methods and protocols, Morgan, J.R. and Yarmush, M. L.,, eds. Humana Press, Totowa, N. J., 553-575, 1999.

Jain, R. K., "*Angiogenesis and Lymphangiogensis in Tumors: Insights from Intravital Microscopy*," Cold Spring Harb. Symp. Quant. Biol., 67, 239-248, 2002.

Murdin et al., "*Immobilisation and Growth of Hybridomas in Packed Beds*," Bioreactors and Biotransformations, Moody, G. W. and Baker, P. B., eds. Elsevier Applied Science Publishers, London, New York, 99-110, 1987.

Allen et al, "*Improving the Next Generation of Bioartificial Liver Devices*," Seminars in Cell & Developmental Biology, 13, 447-454, 2002.

Augenstein et al., "*Effect of Shear on Death of Two Strains of Mammalian Tissue Cells*," Biotechnol. Bioeng. , 13, 409-418, 1971.

Beeton et al., "*A Novel Membrane Bioreactor for Microbial-Growth*," Appl. Microbiol. Biotechnol. , 40, 812-817, 1994.

Bhujwalla et al., "*Combined Vascular and Extracellular PH Imaging of Solid Tumors*," NMR Biomed., 15,114-119, 2002.

Black et al., "*Diblock Copolymers: Self-Assembly for Applications in Microelectronics*," Encyclopedia of Materials : Science and Technology, Buschow, KHJ, ed. Elsevier, New York, 1-6, 2002.

Black et al., "Tuominen, M. T. , Integration of Self-Assembled Diblock Copolymers for Semiconductor Capacitor Fabrication," Appl. Phys. Lett., 79, 409-411, 2001.

Borenstein et al., "*Microfabrication Technology for Vascularized Tissue Engineering, Biomedical Microdevices*," 4, 167-175, 2002.

Boyden, S., "*The Chemotactic Effect of Mixtures of Antibody and Antigen on Polymorphonuclear Leucocytes*," J. Exp. Med., 115, 453-466, 1962.

Brown et al., "*Improvements to Parallel Plate Flow Chambers to Reduce Reagent and Cellular Requirements*," BMC Immunology, 2, 9-16, 2001.

Cinamon et al., "*A Real Time in Vitro Assay for Studying Leukocyte Transendothelial Migration Under Physiological Flow Conditions*," J. Immunol. Methods, 273, 53-62, 2003.

De Bartolo et al., "*A Novel Full-Scale Flat Membrane Bioreactor Utilizing Porcine Hepatocytes: Cell Viability and Tissue-Specific Functions*," Biotechnol. Prog. , 16,102-108, 2000.

Ding et al., "*Chemokines Stimulate Human T Lymphocyte Transendothelial Migration to Utilize VLA-4 in Addition to LFA-1*," J. Leukoc. Biol., 69, 458-466, 2001.

Drioli et al., "*Biocatalytic Membrane Reactors, Applications in Biotechnology and the Pharmaceutical Industry*," Taylor & Francis, London, Philadelphia, 1999.

Dupin et al., "Impact of Colony Morphologies and Disinfection on Biological Clogging in Porous Media," Environ. Sci. Technol., 34, 1513-1520, 2000.

Dupin et al., "Mesoscale and Microscale Observations of Biological Growth in a Silicon Pore Imaging Element," Environ. Sci. Technol., 33, 1230-1236, 1999.

Falk et al., "*A 48-Well Micro Chemotaxis Assembly for Rapid and Accurate Measurement of Leukocyte Migration*," J. Immunol. Methods, 33, 239-247, 1980.

Fink et al., "*Chronic Stretch of Engineered Heart Tissue Induces Hypertrophy and Functional Improvement*," FASEB J., 14, 669-679, 2000.

Folkman et al., "*Tumor Angiogenesis—Therapeutic Implications*," N. Engl. J. Med., 285, 1182-1186, 1971.

Gillies et al., "*MRI of the Tumor Microenvironment*," J. Magn. Reson. Imaging, 16, 430-450, 2002.

Godbey et al., "*In Vitro Systems for Tissue Engineering*", Ann. N. Y. , Acad. Sci. , 961,10-26, 2002.

Griffith et al., "*Tissue Engineering—Current Challenges and Expanding Opportunities*," Science, 295, 1009-1014, 2002.

Griffith, L. G., "*Emerging Design Principles in Biomaterials and Scaffolds for Tissue Engineering*," Reparative Medicine: Growing Tissues and Organs, 961, 83-95, 2002.

Guarini et al., "*Nanoscale Patterning Using Self-Assembled Polymers for Semiconductor Applications*," J. Vac. Sci. & Tech. B, 19,2784-2788, 2001.

Guarini et al., "*Optimization of Diblock Copolymer Thin Film Self Assembly*," Advanced Materials, 14,1290-1294, 2002.

Guarini et al., "*Process Integration of Self-Assembled Polymer Templates into Silicon Nanofabrication*," Journal of Vacuum Science & Technology B, 20, 2788-2792, 2002.

Hammer et al., "*Measuring Receptor-Mediated Cell Adhesion Under Flow: Cell-Free Systems*," Tissue engineering methods and protocols, Morgan, J. R. and Yarmush, M. L. , eds. Humana Press, Totowa, N. J., 543-552, 1999.

Heidemann et al., "*Angiogenic Effects of Interleukin 8 (CXCL8) in Human Intestinal Microvascular Endothelial Cells Are Mediated by CXCR2*," J. Biol. Chem., 278, 8508-8515, 2003.

Helmlinger, "*Acid Production in Glycolysis-Impaired Tumors Provides New Insights into Tumor Metabolism*," Clin. Cancer Res., 8, 1284-1291, 2002.

Higgs et al., "*Regulation of Actin Filament Network Formation Through Arp2/3 Complex: Activation by a Diverse Array of Proteins*," Annu. Rev. Biochem., 70, 649-676, 2001.

Hu et al., "*Large-Scale Mammalian Cell Culture*," Curr. Opin. Biotechnol., 8, 148-153, 1997.

Jackman et al., "*Electrochemistry and Soft Lithography: A Route to 3-D*," Chemtech, 29,18-30, 1999.

Jain et al., "*Dissecting Tumour Pathophysiology Using Intravital Microscopy*," Nature Reviews Cancer, 2, 266-276, 2002.

Jones et al., "*P-Selectin Mediates Neutrophil Rolling on Histamine-Stimulated Endothelial Cells*," Biophys. J., 65, 1560-1569, 1993.

Kaihara et al., "*Silicon Micromachining to Tissue Engineer Branched Vascular Channels for Liver Fabrication*," Tissue Eng., 6, 105-117, 2000.

Klemke et al., "*CAS/Crk Coupling Serves as a "Molecular Switch" for Induction of Cell Migration*," Journal of Cell Biology, 140, 961-972, 1998.

Labecki et al., "*Protein Transport in Ultrafiltration Hollow-Fiber Bioreactors for Mammalian Cell Culture*," Membrane Separations in Biotechnology, Wang, W. K., ed., M. Dekker, New York, 1-62, 2001.

Ley, K., "*The Selectins As Rolling Receptors*," The selectins: initiators of leukocyte endothelial adhesion, Vestweber, D, ed. Harwood Academic Publishers, Australia, 63-104, 1997.

Li et al., "*Cortactin Potentiates Bone Metastasis of Breast Cancer Cells*," Cancer Res, 61, 6906-11, 2001.

Li et al., "*Hexagonal Pore Arrays With a 50-420 Nm Interpore Distance Formed by Self-Organization in Anodic Alumina*," J. Appl. Phys., 84, 6023-6026, 1998.

Li et al., "*Initial Stages of Tumor Cell-Induced Angiogenesis: Evaluation Via Skin Window Chambers in Rodent Models*," J Natl Cancer Inst, 92, 143-7, 2000.

Li et al., "*On the Growth of Highly Ordered Pores in Anodized Aluminum Oxide*," Chem. Mater., 10, 2470-2480, 1998.

Lin et al., "*Antiangiogenic Gene Therapy Targeting the Endothelium-Specific Receptor Tyrosine Kinase Tie2*," Proc. Natl Acad Sci U S A, 95, 8829-34, 1998.

Lin et al., "*Inhibition of Tumor Angiogenesis Using a Soluble Receptor Establishes a Role for Tie2*," in Pathologic Vascular Growth, J Clin Invest, 100, 2072-8, 1997.

Lin et al., "*Inhibition of Tumor Growth by Targeting Tumor Endothelium Using a Soluble Vascular Endothelial Growth Factor Receptor*," Cell Growth Differ, 9, 49-58, 1998.

MacNeill et al., "*Toward a New Blood Vessel*," Vasc. Med., 7, 41-246, 2002.

Mansky et al., "*Controlling Polymer-Surface Interactions With Random Copolymer Brushes*," Science, 275, 1458-1460, 1997.

Martinez et al., "*Acidic PH Enhances the Invasive Behavior of Human Melanoma Cells, Clinical & Experimental Metastasis*," 14, 176-186, 1996.

McDonald et al., "*Poly (Dimethylsiloxane) As a Material for Fabricating Microfluidic Devices*," Accounts of Chemical Research, 35, 491-499, 2002.

McDuffie N. G., Cell Culture Bioreactors. In : Bioreactor Design Fundamentals, Butterworth-Heinemann, Boston, 93-119, 1991.

Millward et al., "*The Vortex Wave Membrane Bioreactor: Hydrodynamics and Mass Transfer*," Chemical Engineering Journal and the Biochemical Engineering Journal, 62, 175-181, 1996.

Mooney et al., "*Stabilized Polyglycolic Acid Fibre Based Tubes for Tissue Engineering*," Biomaterials, 17, 115-124, 1996.

Munn et al., "*Analysis of Cell Flux in the Parallel-Plate Flow Chamber-Implications for Cell Capture Studies*," Biophys. J., 67, 889-895, 1994.

Nollert et al., "*Hydrodynamic Shear-Stress and Mass-Transport Modulation of Endothelial-Cell Metabolism*," Biotechnol. Bioeng., 38, 588-602, 1991.

Papadaki et al., "*Quantitative Measurement of Shear-Stress Effects on Endothelial Cells*," Tissue engineering methods and protocols, Morgan, J. R. and Yarmush, M. L., eds. Humana Press, Totowa, N. J., 577-593, 1999.

Park et al., "*Integration of Cell Culture and Microfabrication Technology*," Biotechnol. Prog., 19, 243-253, 2003.

Passeraub et al., "*Design, Microfabrication and Analysis of a Microfluidic Chamber for the Perfusion of Brain Tissue Slices*," Biomedical Microdevices, 5, 147-155, 2003.

Powers et al., "*A Microfabricated Array Bioreactor for Perfused 3D Liver Culture*," Biotechnol. Bioeng., 78, 257-269, 2002.

Ramos et al., "*Quantitative Measurement of Cell-Cell Adhesion Under Flow Conditions*," Tissue engineering methods and protocols, Morgan, J. R. and Yarmush, M. L., eds. Humana Press, Totowa, N. J., 507-519, 1999.

Renard et al., "*Induced Changes of Leukocyte Slow Rolling in an in Flow Pharmacological Model of Adhesion to Endothelial Cells*," Biorheology, 40, 173-178, 2003.

Roth et al., "*Characterization of Transendothelial Chemotaxis of T Lymphocytes*," J. Immunol. Methods, 188, 97-116, 1995.

Schultz, "*Roles of Solute and Heat-Flow in the Development of Polymer Microstructure*," Polymer, 32, 3268-3283, 1991.

Snyder et al., "*Fabrication of Multiple Microscale Features on Polymer Surfaces for Applications in Tissue Engineering*," Biomedical Microdevices, 3, 293-300, 2001.

Solan et al., "*Engineered Vessels: Importance of the Extracellular Matrix*," Transplant. Proc., 33, 66-68, 2001.

Tobert et al., "*Perfusion Culture Systems for Production of Mammalian Cell Biomolecules*," Large-Scale Mammalian cell culture, Feder, J. and Tolbert, W. R., eds., Academic Press, Orlando, 97-123, 1985.

Voisard et al., "*Potential of Cell Retention Techniques for Large-Scale High-Density Perfusion Culture of Suspended Mammalian Cells*," Biotechnol. Bioeng., 82, 751-765, 2003.

Walheim et al., "*Structure Formation Via Polymer Demixing in Spin-Cast Films*," Macromolecules, 30, 4995-5003, 1997.

Weidner et al., "*Tumor Angiogenesis and Metastasis-Correlation in Invasive Breast-Carcinoma*," N. Engl. J. Med., 324, 1-8, 1991.

Whitesides et al., Ingber, D. E., "*Soft Lithography in Biology and Biochemistry*," Annual Review of Biomedical Engineering, 3, 335-373, 2001.

Wu et al. "*Fabrication of Complex Three-Dimensional Microchannel Systems in PDMS*," J. Am. Chem. Soc., 125, 554-559, 2003.

Xia et al., "*Soft Lithography*," Annual Review of Materials Science, 28, 153-184, 1998.

Yao et al., "*Chemotaxis by a CNS Macrophage*," the Microglia, J. Neurosci. Res., 27, 36-42, 1990.

\* cited by examiner

US 7,977,089 B2

BIOREACTORS WITH MULTIPLE CHAMBERS

STATEMENT OF FEDERALLY-SPONSORED RESEARCH

This invention was made with Government support under Contract No. N66001-01 C-8064 awarded by the Defense Advanced Research Projects Administration and the Office of Naval Research. The Government has certain rights in the invention.

CROSS-REFERENCE TO RELATED PATENT APPLICATION

This application is related to co-pending U.S. patent applications of U.S. Ser. No. 10/525,538, entitled "Bioreactors With an Array of Chambers and a Common Feed Line," which status is now pending, U.S. Ser. No. 10/525,559, entitled "Capillary Perfused Bioreactors with Multiple Chambers," which status is now allowed, and U.S. Ser. No. 10/525,648, entitled "Bioreactors with Substance Injection Capacity," which status is now pending. All of the above-identified co-pending applications were filed on Feb. 24, 2005, and have the same assignee as the present application.

This application is being filed as an International Patent application in the name of Vanderbilt University, a U.S. national corporation, applicant for the designation of all countries except the US, and John P. Wikswo and Franz J. Baudenbacher, both U.S. nationals and residents, applicants for the designation of the US only, on 27 Aug. 2003.

Some references, which may include patents, patent applications and various publications, are cited in a reference list and discussed in the description of this invention. The citation and/or discussion of such references is provided merely to clarify the description of the present invention and is not an admission that any such reference is "prior art" to the invention described herein. In terms of notation, hereinafter, "[n]" represents the nth reference cited in the reference list. For example, [11] represents the 11th reference cited in the reference list, namely, Hu, W. S. and Aunins, J. G., Large-Scale Mammalian Cell Culture, Curr. Opin. Biotechnol., 8, 148-153, 1997.

FIELD OF THE INVENTION

The present invention generally relates to an apparatus and methods for growing and maintaining a living system. More particularly, the present invention relates to an apparatus and methods that have a channel configuration allowing perfusate flow with diffusional exchange to tissue cells but no cell migration. Additionally, the present invention relates to an apparatus and methods that have capacity for growing and maintaining a living microorganism such as protozoa.

The present invention also relates to an apparatus and methods for dynamic analysis of a collection of cells such as a biofilm. More particularly, the present invention relates to an apparatus and methods for measuring response of a biofilm to one or more dynamic streams of substance such as chemical stressors at various depths of the biofilm.

Certain embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise bioreactors with multiple chambers and methods of using the same.

Certain other embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise bioreactors with an array of chambers with a common feed line and methods of using the same.

Certain additional embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise capillary perfused bioreactors and methods of using the same.

Certain further embodiments of the present invention comprise apparatus and methods for growing and maintaining a living system such as a cell or a collection of cells and monitoring the status of such a living system that is metabolically active and responsive to environmental change, wherein each metabolic activity of the cell may be characterized by a characteristic time. More particularly, the apparatus and methods comprise bioreactors with substance injection capability and methods of using the same.

BACKGROUND OF THE INVENTION

Bioreactor is a device that can be used for culturing living cells. More particularly, bioreactors are vessels that provide a proper physical and chemical environment as well as fast transport of substrates and products to allow cellular biological reactions to occur, ideally rapidly and efficiently. The simplest bioreactor is a culture dish: In conventional cell culture using well-plates, culture-dishes, and flasks, the volume of the culture medium is typically 200 to 1000 times the volume of the cells. This ratio, when used in combination with buffering of the culture media, allows the cells to grow for at least 24 hours without media change. However, another consequence of this ratio is a corresponding dilution of whatever extracellular factors are produced by the cells and might otherwise provide paracrine cell-to-cell communication, which is possible in tissue because the extracellular volume might be only 10% of intracellular volume.

Much of the development of bioreactors was directed towards either the functional tissues, or the generation of biochemicals and pharmaceuticals. For example, over the last 20 years studies on the generation of skin, pancreas, cartilage, liver, cornea and bladder have taken particular importance[1]. In the United States alone, there are more than 80,000 individuals waiting for an organ transplant, and hence the need to develop improved bioreactor technology is self-evident. There is also a growing recognition that progress in understanding cell motility and chemotactic signaling, as well as other complex cellular processes, is often constrained by the laboratory techniques available for observing and intervening at various points in the processes. Many of these processes can be examined best in a properly instrumented bioreactor.

There is a wide variety in bioreactors, including stirred vessels, bubble column, packed beds[2], air-lift reactors, and membrane reactors[3] that include plates, rotating plates, spiral-wound and hollow fibres. Hollow-fiber reactors are of special importance since (depending of their structure) they may allow as much as 30,000 m² of membrane area per m³ module volume[4-6]. However, given that mammalian cells are very sensitive to shear forces[7-9] (which originate mainly from agitation and aeration), it is important to reduce the forces as much as possible in the reactor where the cells will be grown[9,10]. Membranes have been used in bioreactors to increase survival of cells. For instance, it has been known that liquid-gas interface created in some models of reactors is particularly damaging for mammalian cells. That potentially lethal interface can be eliminated by the use of a hydrophobic membrane[9].

Bioreactors may be also classified by means of their mode of operation: batch, fed-batch and continuous cultivation (also called perfused cultivation). In the first or batch mode, no substrate is added, nor medium removed; in the case of the fed-batch mode there is a continuous feeding, but nothing is removed until the reactions are terminated and the reactor emptied. While these systems imply a low effort for process control, the productivity is low compared to that in perfused systems, the third mode, where a permanent inflow of substrate and outflow of medium takes place. Besides the high productivity, there is a better cell physiology control in this kind of reactors[11] and in the case of mammalian cell culture, it has been shown to provide significant advantage over static methods[12,13].

One of the limitations when developing large three-dimensional tissues is the lack of a proper vascular supply for nutrient and metabolite transport. A number of studies have analyzed the artificial vascular networks[14-18], and there have been a number of attempts to construct functional microfabricated scaffolds[3,16,19-21]. The techniques by which these networks have been produced include plasma etching, photolithography, soft lithography, microcontact printing, microfluidic patterning using microchannels, laminar flow patterning and stencil patterning[22-25]. In the case of plasma etching technologies we can consider the high aspect ratio micromachining (HARMS) as a very powerful tool since it allows to etch channels of virtually unlimited depth without increasing the width already achieved by lithography[22]. It is also possible to construct three dimensional microchannel systems in PDMS with complex topologies and geometries[15].

Additionally, one needs to realize that the growth of clinically-implantable tissue may require the ultimate biodegradation and the mechanical properties of the tissue scaffold[16]. These properties are directly related to the crystallinity, molecular weight, glass transition temperature and monomer hydrophobicity of the materials chosen to fabricate the tissue[19]. Naturally derived materials such as collagen have been employed[26], as well as synthetic and semi synthetic ones. Polyglycolic acid (PGA) possesses high porosity and it makes easy the fabrication of devices, therefore, PGA fibre meshes have been considered to transplant cells. However, they cannot resist significant compressional forces. An alternative to solve this problem is to use polymers of lactic and glycolic acid whose ratios can be adjusted to control the crystallinity of the material and hence the degradation rate and mechanical properties. Fibre-based tubes have been fabricated from these polymers[27].

It is important to compare the vascular nature of living tissue with the capabilities provided by existing microfabricated cell-perfusion bioreactor systems. In tissue, arteries divide into progressively smaller vessels, eventually reaching arterioles and then capillaries. The arterioles are important because they contain the precapillary sphincters, which allow control of the perfusion of individual capillary beds, but also provide the majority of the peripheral resistance and hence the pressure drop associated with the arterial supply. As a result, the pressure difference across the capillary endothelium membrane is kept sufficiently low to allow diffusional transport of nutrients and metabolites across the membrane, as well as the trafficking of immune cells required for tissue maintenance and infection control. Were the pressures in the capillaries as high as those in the arterioles, the capillary wall thickness would be too great to allow these critical transport phenomena. The venous return system is in many ways a mirror of the arterial system, albeit at lower pressures. Another feature of the living vascular system is that the branching process described above allows all cells to be within 50 to 200 microns of a capillary, depending upon the specific tissue. As a result, the arterial supply and venous return systems are intercalated in such a manner that every capillary that perfuses a large group of cells is connected to the larger supply and return systems with a self-similarity that ensures uniform perfusion and transcapillary pressures. It is this intercalation process that is so difficult to replicate with microfabrication. For example, Borenstein et al.,[22] describe a process to build a two-dimensional vascular system that could create a multi-scale perfusion system for supporting endothelial cells, but there is no provision to selectively limit diffusive transport across the smallest capillaries to perfuse cells lying outside of the perfusion network. More importantly, the networks they show have a large region of the device that is covered with the larger vessels, and the region of the bioreactor that is limited to capillary vessels is in fact quite small.

Thus, there is a need for microfabricated migration bioreactors that mimic in vitro the microenvironments of normal tissue was well as that of tumors, infected tissue, and wounded tissue, while providing independent control of chemokine and growth factor gradients, shear forces, cellular perfusion, and the permeability of physical barriers to cellular migration, thereby allowing detailed optical and electrochemical observation of normal, immune, and cancerous cells during cell migration, intravasation, extravasation, and angiogenesis. Angiogenesis, tumor metastasis, and leukocyte infiltration into tissue are complex processes that are regulated not only by cellular responses to a single chemokine, but also by external factors, such as multiple competing chemokine and growth factor signals, autocrine feedback loops, cell-cell interactions, and mechanical forces such as vessel shear stress. Current approaches for assessing migration across cellular barriers include Boyden and transwell chambers that provide an integrated fluorescence assay of migration across filters to allow quantitation of migration[28-34], parallel plate flow chambers[35-38], in which adhesion and rolling on endothelial cells in shear stress can be assessed[35,39-44], and in vivo intravital microscopy in which migration of cells in living animals is visualized[45-48]. Each of these approaches has limitations, including the inability to have sustained and controlled chemotactic gradients (all systems), the inability to visualize migration in real time or with physiologic shear stress (Boyden and transwell chambers), the inability to observe extravasation or angiogenesis into an underlying, deep cellular matrix (parallel plate flow chambers) and the inability to control all aspects of the experiments, e.g., having defined cell populations and controlled microfluidics for independent control of shear and tissue perfusion (all systems, especially intravital microscopy). The development of a motility/metastasis model system with independent control of endothelial shear stress, chemokine gradients, tissue perfusion, and the ability to add different cell types through different ports, combined with state-of the art imaging techniques and sensor capabilities would represent a huge advance over currently available systems.

Indeed, the need for such capabilities is quite urgent. Angiogenesis is a dynamic process, influenced by the cellular microenvironment and intricately linked to metastasis[49,50]. It has been demonstrated that both VEGF and angiopoietin/tyrosine kinase (Ang/Tie2) function are required for tumor angiogenesis[51-53]. However, how signals from those two receptor systems are integrated to mediate angiogenesis has not been determined, in part due to the lack of good model systems. The next step would be to study the coordination and integration of VEGF and Ang signaling in endothelial cell migration, vascular sprouting and maturation, and tumor transendothelium migration. As with angiogenesis, multiple environmental inputs affect tumor metastasis and leukocyte infiltration. Activation of one chemokine receptor in tumor cells affects the induction of other ligands and receptors in tumor cells as well as endothelial cells and leukocytes, but the mechanism is poorly understood[54]. There is a need for an understanding of how alteration of chemokine receptor internalization and/or changes in receptor association with adaptor molecules such as AP-2 or beta-arresting affect chemokine receptor activity as tumor cells move through a complex matrix. How external factors such as cell-cell adhesion, cell-matrix interactions, and vessel shear stress affect cytoskeletal reorganization during migration through tissues is also poorly understood. Cortactin overexpression increases the metastasis of breast cancer cells to bone[55], however the mechanism remains unclear. Likewise, lack of WASp protein in humans leads to an X-linked immune disorder that may result from signaling, proliferation or chemotaxis defects[56]. There is a need to study the role of cortactin and WASp proteins in chemotaxis of breast cancer and HL60 cells in a complex multicell environment involving controllable shear, cell-cell interactions, and chemokine gradients. As a final example, matrix metalloproteinases (MMPs) are extracellularly expressed enzymes found in many types of cancer and are thought to be important in tumor development, growth, invasion and metastasis. It has recently been discovered that skin tumors that develop in mice deficient for MMP-3 (MMP-3 null mice) progress and grow much faster than skin tumors from normal, wild-type mice. This difference is associated with a reduced number of immune cells in the tumor and surrounding tissue in the MMP-3 null mice. The logical progression of this research is to determine how loss of an MMP affects the ability of immune cells, namely monocytes and neutrophils, to infiltrate from the peripheral blood circulation to the tumor site. The ability to control the experimental environment, including multiple defined cell populations, is critical to elucidate the relative importance of tumor-host interactions in MMP-3 induced cellular chemotaxis.

Despite the progress made over the years, however, currently available bioreactors cannot provide a more physiologic environment that would include a three-dimensional in vitro region with multiple cell types, stimuli, and measurement capabilities and allows study of molecular aspects of the chemotactic response. Thus, bioreactors that mimic in vitro the microenvironments of tumors and tissue while providing independent control of chemokine and growth factor gradients, shear forces, cellular perfusion, and the permeability of physical barriers to cellular migration, thereby allowing detailed optical and electrochemical observation of normal and cancerous cells during cell migration, intravasation, extravasation, and angiogenesis need to be developed.

Therefore, a heretofore unaddressed need exists in the art to address the aforementioned deficiencies and inadequacies.

SUMMARY OF THE INVENTION

In one aspect, the present invention relates to a bioreactor for cultivating living cells in a liquid medium. In one embodiment, the bioreactor has a first substrate having a first surface and an opposite second surface, defining a chamber therebetween for receiving the cells and the liquid medium. The bioreactor further has a barrier dividing the chamber into a first subchamber and a second subchamber, wherein the barrier has a porosity to allow the first subchamber and the second subchamber in fluid communication and allow at least one predetermined type of cells to permeate between the first subchamber and the second subchamber.

As formed, the first subchamber is adapted for receiving a first type of material and the second subchamber is adapted for receiving a second type of material, wherein each of the first type of material and the second type of material contains at least one selected from the group of cells, chemicals, and fluids. The cells can be any type of living cells, including, but not limited to, bacteria, protozoa, or both, normal cells, tumor cells, or any combination of them.

The bioreactor also includes a biocompatible coating layer applied to the chamber walls, wherein the biocompatible coating layer comprises a material that may inhibit cell adhesion to the biocompatible coating layer, enhance cell adhesion to the biocompatible coating layer, or function as a fluorescent marker or indicator of the state of cells.

At least one inlet port and an input transfer channel are formed in the first substrate, wherein the input transfer channel is in fluid communication with the inlet port and one of the first subchamber and the second subchamber for allowing delivery of the cells, fluids or chemicals to the corresponding subchamber. At least one outlet port and an outlet transfer channel are also formed in the first substrate, wherein the outlet transfer channel is in fluid communication with the outlet port and one of the first subchamber and the second subchamber for allowing removal of the cells, fluids or chemicals from the corresponding subchamber. Additionally, at least one auxiliary port and an auxiliary channel are formed in the first substrate, wherein the auxiliary channel is in fluid communication with the auxiliary port and one of the input transfer channel and the outlet transfer channel for flushing the corresponding transfer channel. Furthermore, at least one access port and an access channel are formed in the first substrate, wherein the access channel is in fluid communication with the access port and one of the first subchamber and the second subchamber for allowing delivery or removal of the cells, fluids, chemicals, coating material or sensing material to the corresponding subchamber.

The bioreactor further includes a second substrate, wherein the second substrate is positioned adjacent to the first surface of the first substrate and defines a plurality of connection channels, each of the connection channels being formed so as to be in fluid communication with a corresponding one of the inlet port, the outlet port, the auxiliary port, and the access port. The bioreactor additionally has a plurality of connection ports, each of the connection ports being formed with a channel and being positioned to the second substrate such that each channel of the connection ports is in fluid communication with a corresponding one of the connection channels formed in the second substrate.

In one embodiment, the first substrate is fabricated from glass, Mylar, PDMS, silicon, a polymer, a semiconductor, or any combination of them. The barrier comprises a porous material, wherein the barrier is microfabricated so as to form a structure allowing the fluid communication between the first subchamber and the second subchamber.

The bioreactor additionally includes a third substrate, wherein the third substrate is positioned adjacent to the second surface of the first substrate, and means positioned in the third substrate and adapted for electrochemical measurements of the cells responsive to the liquid medium in at least one of the first subchamber and the second subchamber. The third substrate can be formed with a semiconductor material such as silicon.

In one embodiment, the means for electrochemical measurements includes a reference electrode, a counter electrode, a plurality of edge connector pads, and a plurality of electrically conductive leads, wherein a first electrically conductive lead electrically couples the reference electrode to a corresponding edge connector pad, and a second electrically conductive lead electrically couples the counter electrode to a corresponding edge connector pad. The means for electrochemical measurements further includes a plurality of individually addressable working electrodes, each being electrically coupled to a corresponding edge connector pad through a corresponding electrically conductive lead, wherein the liquid medium includes at least one or more analytes, and wherein the plurality of individually addressable working electrodes are adapted to be capable of sensing the concentration of a single analyte of the liquid medium at multiple locations in the chamber or the concentrations of a plurality of analytes of the liquid medium at multiple locations in the chamber at a time period shorter than a characteristic reaction time related to at least one of cellular physiological activities of the cells. Additionally, the plurality of individually addressable working electrodes are further adapted to be capable of measuring the metabolic variables related to the cells responsive to the liquid medium at multiple locations in the chamber at a time period shorter than a characteristic reaction time related to at least one of cellular physiological activities of the cells.

The bioreactor further includes a fourth substrate, wherein the fourth substrate is positioned above the second surface of the first substrate, and means positioned in the fourth substrate and adapted for optical measurements of the cells responsive to the liquid medium in at least one of the first subchamber and the second subchamber. The fourth substrate is at least partially transparent. The fourth substrate can be formed with a semiconductor material such as silicon.

In one embodiment, the means for optical measurements includes a plurality of optical sensors, a plurality of edge connector pads, and a plurality of leads, each optically coupling an optical sensor to a corresponding edge connector pad, wherein the plurality of optical sensors comprises at least one device selected from the group of an LED and photodiode pair, a fiber optic coupler, and an optical detecting head, wherein the liquid medium includes at least one or more analytes, and wherein the plurality of optical sensors are adapted to be capable of sensing the concentration of a single analyte of the liquid medium at multiple locations in the chamber or the concentrations of a plurality of analytes of the liquid medium at multiple locations in the chamber at a time period shorter than a characteristic reaction time related to at least one of cellular physiological activities of the cells. Additionally, the plurality of optical sensors are further adapted to be capable of measuring the metabolic variables related to the cells responsive to the liquid medium at multiple locations in the chamber at a time period shorter than the characteristic reaction time related to at least one of cellular physiological activities of the cells.

In another aspect, the present invention relates to a bioreactor for cultivating living cells in a liquid medium. In one embodiment, the bioreactor has a substrate having a first surface and an opposite second surface, defining a chamber therebetween for receiving the cells and the liquid medium, wherein the chamber is formed with a center and a boundary, a first barrier enclosing the center and a portion of the chamber to form a central chamber, and a second barrier positioned between the first barrier and the boundary so as to form an intermediate chamber and an outer chamber, wherein the first barrier has a first porosity to allow the central chamber and the intermediate chamber in fluid communication and allow at least a first predetermined type of cells to permeate between the central chamber and the intermediate chamber, and the second barrier has a second porosity to allow the outer chamber and the intermediate chamber in fluid communication and allow at least a second predetermined type of cells to permeate between the outer chamber and the intermediate chamber.

As formed, the central chamber is adapted for receiving a first type of material, the intermediate chamber is adapted for receiving a second type of material, and the outer chamber is adapted for receiving a third type of material, wherein each of the first type of material, the second type of material and the third type of material contains at least one selected from the group of cells, chemicals, and fluids. The first predetermined type of cells includes tumor cells, which normally is received in the central chamber corresponding to a tumor space. The second predetermined type of cells includes normal tissue cells, which normally is received in the intermediate chamber corresponding to a tissue space, wherein the outer chamber is corresponding to a vascular space adapted for receiving endothelial cells, macrophage cells, neutophil cells, any combination of them, or other immune cell type.

The bioreactor further has a biocompatible coating layer applied to the chamber walls at the boundary, wherein the biocompatible coating layer includes a material that may inhibit cell adhesion to the biocompatible coating layer, enhance cell adhesion to the biocompatible coating layer, or function as a fluorescent marker or indicator of the state of cells.

At least one additional inlet or outlet port and an input or output transfer channel are formed in the substrate, wherein the input or output transfer channel is in fluid communication with the corresponding inlet or outlet port and the external chamber for allowing delivery of the cells, fluids or chemicals to the outer chamber. Additionally, at least one inlet or outlet port and an input or output transfer channel are formed in the substrate, wherein the input or output transfer channel is in fluid communication with the inlet or outlet port and the central chamber for allowing delivery of the cells, fluids or chemicals to the central chamber.

Moreover, at least one another inlet or outlet port and an input or output transfer channel are formed in the substrate, wherein the input or output transfer channel is in fluid communication with the inlet or outlet port and the intermediate chamber for allowing delivery of the cells, fluids or chemicals to the intermediate chamber.

In one embodiment, the substrate is fabricated from glass, Mylar, PDMS, silicon, a polymer, a semiconductor, or any combination of them. The first barrier includes a porous material, wherein the first barrier is microfabricated so as to form a first structure allowing the fluid communication between the central chamber and the intermediate chamber. The second barrier includes a porous material, wherein the second barrier is microfabricated so as to form a second structure allowing the fluid communication between the outer chamber and the intermediate chamber, and the second structure is different from the first structure. In this embodiment, the first barrier is substantially circular, the second barrier is substantially circular, and the boundary is substantially circular. Alternatively, each of the first barrier, the second barrier, and the boundary can be formed with other geometric shapes.

The bioreactor further includes means adapted for electrochemical measurements of the cells responsive to the liquid medium in at least one of the outer chamber, the intermediate chamber and the central chamber, wherein the means for electrochemical measurements includes a reference electrode, a counter electrode, and a plurality of individually addressable working electrodes, wherein the liquid medium includes at least one or more analytes.

The plurality of individually addressable working electrodes include a first group of individually addressable working electrodes adapted to be capable of sensing the concentration of a single analyte of the liquid medium at multiple locations in the outer chamber or the concentrations of a plurality of analytes of the liquid medium at multiple locations in the outer chamber at a time period shorter than a characteristic reaction time related to at least one of cellular physiological activities of the cells. The first group of individually addressable working electrodes are further adapted to be capable of measuring the metabolic variables related to the cells responsive to the liquid medium at multiple locations in the outer chamber at a time period shorter than a characteristic reaction time related to at least one of cellular physiological activities of the cells.

The plurality of individually addressable working electrodes further include a second group of individually addressable working electrodes adapted to be capable of sensing the concentration of a single analyte of the liquid medium at multiple locations in the central chamber or the concentrations of a plurality of analytes of the liquid medium at multiple locations in the central chamber at a time period shorter than a characteristic reaction time related to at least one of cellular physiological activities of the cells. The second group of individually addressable working electrodes are further adapted to be capable of measuring the metabolic variables related to the cells responsive to the liquid medium at multiple locations in the central chamber at a time period shorter than a characteristic reaction time related to at least one of cellular physiological activities of the cells.

The plurality of individually addressable working electrodes additionally has a third group of individually addressable working electrodes adapted to be capable of sensing the concentration of a single analyte of the liquid medium at multiple locations in the intermediate chamber or the concentrations of a plurality of analytes of the liquid medium at multiple locations in the intermediate chamber at a time period shorter than a characteristic reaction time related to at least one of cellular physiological activities of the cells. The third group of individually addressable working electrodes are further adapted to be capable of measuring the metabolic variables related to the cells responsive to the liquid medium at multiple locations in the intermediate chamber at a time period shorter than a characteristic reaction time related to at least one of cellular physiological activities of the cells.

In yet another aspect, the present invention relates to a bioreactor for cultivating living cells in a liquid medium. In one embodiment, the bioreactor includes a substrate having a first surface and an opposite second surface, defining a chamber therebetween for receiving the cells and the liquid medium with a boundary, and means for dividing the chamber into plurality of chambers, wherein each of the plurality of subchambers is in fluid communication with at least another one of the plurality of subchambers.

The dividing means includes a barrier to divide the chamber into a first subchamber and a second subchamber, and wherein the barrier has a porosity to allow the first subchamber and the second subchamber in fluid communication and allow at least one predetermined type of cells to permeate between the first subchamber and the second subchamber.

Alternatively, the dividing means includes a first barrier and a second barrier to divide the chamber into a first subchamber, a second subchamber and a third subchamber, and wherein the first barrier has a first porosity to allow the first subchamber and the intermediate subchamber in fluid communication and at least a first predetermined type of cells to permeate between the first subchamber and the second subchamber, and the second barrier has a second porosity to allow the second subchamber and the third subchamber in fluid communication and at least a second predetermined type of cells to permeate between the second subchamber and the third subchamber, wherein the first porosity and the second porosity can be same or different.

Further alternatively, the dividing means includes a plurality of n barriers, n being an integer greater than zero, to divide the chamber into n+1 subchambers, wherein each of n barriers has a corresponding porosity that can be same or different from that of other barriers.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1A:
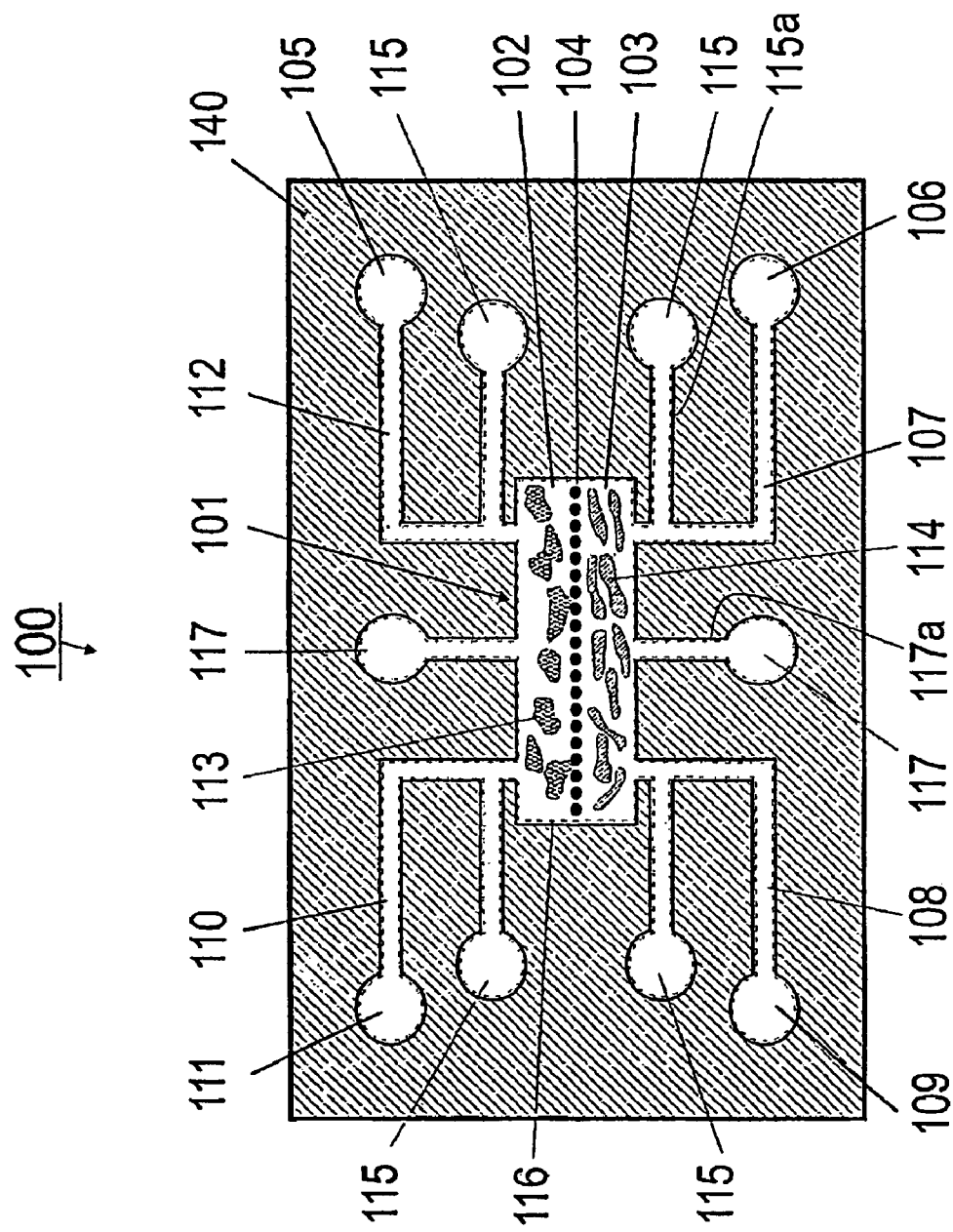
FIG. 1A schematically shows a top view of a bioreactor according to one embodiment of the present invention.

Various embodiments of the invention are now described in detail. Referring to the drawings, like numbers indicate like parts throughout the views unless the context clearly dictates otherwise. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

Definitions

The terms used in this specification generally have their ordinary meanings in the art, within the context of the invention, and in the specific context where each term is used. For example, conventional techniques of molecular biology, microbiology and recombinant DNA techniques may be employed in accordance with the present invention. Such techniques and the meanings of terms associated therewith are explained fully in the literature. See, for example, Sambrook, Fitsch & Maniatis. Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994). See also, PCR Protocols: A Guide to Methods and Applications, Innis et al., eds., Academic Press, Inc., New York (1990); Saiki et al., Science 1988, 239:487; and PCR Technology: Principles and Applications for DNA Amplification, H. Erlich, Ed., Stockton Press.

Certain terms that are used to describe the invention are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

The term "molecule" means any distinct or distinguishable structural unit of matter comprising one or more atoms, and includes for example polypeptides and polynucleotides.

As used herein, "cell" means any cell or cells, as well as viruses or any other particles having a microscopic size, e.g. a size that is similar to that of a biological cell, and includes any prokaryotic or eukaryotic cell, e.g., bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. As used herein, a cell is generally living unless otherwise indicated. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate). Cell or a plurality of cells can also comprise cell lines. Example of cell lines include liver cell, macrophage cell, neuroblastoma cell, endothelial cell, intestine cell, hybridoma, CHO, fibroblast cell lines, red blood cells, electrically excitable cells, e.g. Cardiac cell, myocytes (AT1 cells), cells grown in co-culture, NG108-15 cells (a widely used neuroblastoma X glioma hybrid cell line, ATCC# HB-12317), primary neurons, a primary cardiac myocyte isolated from either the ventricles or atria of an animal neonate, an AT-1 atrial tumor cardiac cell, Liver cells are also known as Hepatocytes, Secretory cell (depolarize and it secretes things) pancreatic beta cells secrete insulin, HELA cells (Helen Lane), HEK293 Human Epithial Kidney c, Erythrocytes (primary red blood cells), Lymphocytes and the like. Each cell line may include one or more cells, same or different. For examples, the liver cell comprises at least one of Human hepatocellular carcinoma ("HEPG2") cell, CCL-13 cell, and H4IIE cell, the macrophage cells comprises at least one of peripheral blood mononuclear cells ("PBMC"), and skin fibroblast cells, the neuroblastoma cell comprises a U937 cell, the endothelial cell comprises a human umbilical vein-endothelial cell ("Huv-ec-c"), and the intestine cell comprises a CCL-6 cell.

"Culture" means a growth of living cells in a controlled artificial environment. It may be a culture of microorganisms, such as a bacterial culture, or one of animal or plant cells, such as a tissue culture. The bioreactors according to the invention can do both and more. Cultures require appropriate sources of food and energy, provided by the culture medium, and a suitable physical environment. Tissue cultures can themselves become a culture medium for viruses, which grow only with live cells. Cultures of only one kind of cells are known as pure cultures, as distinguished from mixed or contaminated cultures.

"Tissue" means an aggregation of cells more or less similar morphologically and functionally. The animal body is composed of four primary tissues, namely, epithelium, connective tissue (including bone, cartilage, and blood), muscle, and nervous tissue. The process of differentiation and maturation of tissues is called histogenesis.

A "sensor" is broadly defined as any device that can measure a measurable quantity. For examples, a sensor can be a thermal detector, an electrical detector, a chemical detector, an optical detector, an ion detector, a biological detector, a radioisotope detector, an electrochemical detector, a radiation detector, an acoustic detector, a magnetic detector, a capacitive detector, a pressure detector, an ultrasonic detector, an infrared detector, a microwave motion detector, a radar detector, an electric eye, an image sensor, any combination of them and the like. A variety of sensors can be chosen to practice the present invention.

The term "analyte" means a material that can be consumed or produced by a cell. Examples of analyte of interest include pH, K, oxygen, lactate, glucose, ascorbate, serotonin, dopamine, ammonina, glutamate, purine, calcium, sodium, potassium, NADH, protons, insulin, NO (nitric oxide) and the like.

The term "flow" means any movement of fluid such as a liquid or solid through a device or in a method of the invention, and encompasses without limitation any fluid stream, and any material moving with, within or against the stream, whether or not the material is carried by the stream. For example, the movement of molecules or cells through a device or in a method of the invention, e.g. through channels of a substrate on microfluidic chip of the invention, comprises a flow. This is so, according to the invention, whether or not the molecules or cells are carried by a stream of fluid also comprising a flow, or whether the molecules or cells are caused to move by some other direct or indirect force or motivation, and whether or not the nature of any motivating force is known or understood. The application of any force may be used to provide a flow, including without limitation, pressure, capillary action, electroosmosis, electrophoresis, dielectrophoresis, optical tweezers, and combinations thereof, without regard for any particular theory or mechanism of action, so long as molecules or cells are directed for detection, measurement or sorting according to the invention.

A "liquid or medium" is a fluid that may contain one or more substances that affecting growth of cells, one or more analytes, or any combination of them. A medium can be provided with one or more analytes to be consumed by one or more cells. A medium can have one or more analytes generated by one or more cells. A medium can also have at the same time one or more analytes to be consumed by one or more cells and one or more analytes generated by one or more cells. A medium may consist of natural materials, such as enzymatic digests, extracts of yeast or beef, milk, potato slices, or chick embryos. Artificial media are prepared by mixing various ingredients according to particular formulas. A complex medium contains at least one crude ingredient derived from a natural material, hence of unknown chemical composition. A chemically defined or synthetic medium is one in which the chemical structure and amount of each component are known.

An "inlet region" is an area of a bioreactor that receives molecules or cells or liquid. The inlet region may contain an inlet port and channel, a well or reservoir, an opening, and other features which facilitate the entry of molecules or cells into the device. A bioreactor may contain more than one inlet region if desired. The inlet region is in fluid communication with the channel and is upstream therefrom.

An "outlet region" is an area of a bioreactor that collects or dispenses molecules or cells or liquid. An outlet region is downstream from a discrimination region, and may contain outlet channels or ports. A bioreactor may contain more than one outlet region if desired.

An "analysis unit" is a microfabricated substrate, e.g., a microfabricated chip, having at least one inlet region, at least one channel and chamber, at least one detection region and at least one outlet region. A device of the invention may comprise a plurality of analysis units.

A "channel" is a pathway of a bioreactor of the invention that permits the flow of molecules or cells to pass a detection region for detection (identification), or measurement. The detection and discrimination regions can be placed or fabricated into the channel. The channel is typically in fluid communication with an inlet port or inlet region, which permits the flow of molecules or cells or liquids into the channel. The channel is also typically in fluid communication with an outlet region or outlet port, which permits the flow of molecules or cells or liquid out of the channel. The channel can also be used as a chamber to grown cells, and vice versa.

A "detection region" or "sensing volume" or "chamber" is a location within the bioreactor, typically in or coincident with the channel (or a portion thereof and/or in or coincident with a detection loop, where molecules or cells to be grown, identified, characterized, hybridized, measured, analyzed or maintained (etc.), are examined on the basis of a predetermined characteristic. In one embodiment, molecules or cells are examined one at a time. In other embodiments, molecules, cells or samples are examined together, for example in groups, in arrays, in rapid, simultaneous or contemporaneous serial or parallel arrangements, or by affinity chromatography.

"Reaction time" is the time that a system of interest requires to respond to a change. For example, the reaction time of a cell is the time required for at least one of the physiological processes of a cell to adapt or respond to a change in its environment. Each type of cell has its own characteristic reaction time with respect to a particular change in its environment. The reaction time of a sensor is the time required for the sensor to respond to a change in the quantity that it is sensing. For example, the reaction time of an electrochemical sensor is set by the size of the sensor and the thickness and nature of protective coatings on the activated surfaces of the sensor. The reaction time of a microfluidic system is determined by, among other things, the reaction time of the cell to changes in the environment, the time required for chemical species to diffuse throughout the sensing volume, the reaction time of the sensor(s) and the diffusion time of the analyte being controlled by the actuators.

"Bacteria" are extremely small—usually 0.3-2.0 micrometers in diameter—and relatively simple microorganisms possessing the prokaryotic type of cell construction. Each bacterial cell arises either by division of a preexisting cell with similar characteristics, or through combination of elements from two such cells in a sexual process.

"Protozoa" means a group of eukaryotic microorganisms traditionally classified in the animal kingdom. Although the name signifies primitive animals, some Protozoa (phytoflagellates and slime molds) show enough plantlike characteristics to justify claims that they are plants. Protozoa range in size from 1 to $10^6$ micrometers. Colonies are known in flagellates, ciliates, and Sarcodina. Although marked differentiation of the reproductive and somatic zooids characterizes certain colonies, such as Volvox, Protozoa have not developed tissues and organs.

Several embodiments are now described with reference to the FIGS. 1-2, in which like numbers indicate like parts throughout the FIGS. 1-2.

Overview of the Invention

The inventors of the present invention overcome the disadvantages of the prior art and develop new bioreactors that have, among other new and inventive features, the capability of providing controlled chemokine gradients independent of the perfusion flow and allow extravasation of a cellular matrix. Recent advances in the fabrication of nanofilters[57,61] are used to create perfused-membrane bioreactors according to the present invention that allow the growth of mixed cultures of cells at near-to-tissue densities in 1 mm×1 mm×100 micron volumes, in the presence of controlled, stable chemokine or growth-factor gradients within the device, to mimic the in vivo tumor microenvironment.

One advantage of the present invention is that custom devices can be constructed such that the isolated perfusion and cell-delivery systems allow independent control of shear stress and chemokine gradients during the course of an experiment. Moreover, the optical and electrochemical metabolic microsensors can be installed within these bioreactors to allow simultaneous quantification of the local metabolic and chemical environment (lactate, pH, $O_2$, etc.) in selected regions within the reactor, while cell migration or cell signaling events are imaged by fluorescence microscopy. Hence, the bioreactors according to the present invention can be considered as the next generation of migration bioreactors that may move beyond a simple MicroTransWell (MTW) system to one that more closely replicates in vitro the microenvironment living tissue.

Moreover, the application of microfabrication techniques, microfluidics, and microbiosensors with the bioreactors according to the present invention offers an opportunity for study of the molecular mechanism of tumor angiogenesis as well as leukocyte and cancer cell extravasation. For example, the systematic examination of the role of Tie2 and VEGF in vascular formation and remodeling and may identify more specific molecular targets for anti-angiogenic therapy. A similar microdevice model could be used to examine leukocyte and cancer cell extravasation. These devices will provide an appropriate cellular environment to host mouse tumor explants, thereby potentially providing a metastasis assay for tumor biopsy material. Metabolic sensing in these bioreactors will help provide a clearer understanding of the tumor microenvironment and confirm the validity of our in vitro systems[62-65].

Additionally, the limitation of the planar Borenstein design that there is too little surface area of capillaries available to support the growth of a substantial volume of cells is overcome by the present invention, which remedies this problem by creating a multi-layer intercalated supply and return bioreactor that allows the full surface of a planar bioreactor to be covered with capillaries, and hence capillary-perfused cells.

More specifically, in one aspect, the present invention relates to bioreactors. These bioreactors are biomicroelectromechanical systems (BioMEMS) that serve as migration microenvironments to study molecular mechanisms of tumor angiogenesis, tumor metastasis and leukocyte migration, but can also function as more general tissue bioreactors and perfusion systems. Among other things, one unique aspect of these microfluidic devices is their integration of suitable cell culture and microfabrication techniques, which permit cell growth in small, confined, well-perfused volumes at tissue densities, provide independent control of multiple chemokines and growth factor gradients, shear forces, tissue perfusion, and permeability of physical barriers to cellular migration, and allow detailed optical and electrochemical observation of normal and cancerous cells during cell migration, intravasation, extravasation, angiogenesis, and other cellular processes.

Recent advances in the fabrication of nanofilters[57-61] can be used to practice the present invention to provide perfused-membrane bioreactors that can allow the growth of mixed cultures of cells at near-to-tissue densities in 1 mm×1 mm×100 micron volumes, in the presence of controlled, stable chemokine or growth-factor gradients within the device, to mimic the in vivo tumor microenvironment. One advantage of the present invention is that custom devices can be constructed such that the isolated perfusion and cell-delivery systems allow independent control of shear stress and chemokine gradients during the course of an experiment. Moreover, the optical and electrochemical metabolic microsensors can be installed within these bioreactors to allow simultaneous quantification of the local metabolic and chemical environment (lactate, pH, $O_2$, etc.) in selected regions within the reactor, while cell migration or cell signaling events are imaged by fluorescence microscopy. Hence the next generation of migration bioreactors will eventually move beyond a simple MicroTransWell (MTW) system to one that more closely replicates in vitro the microenvironment living tissue.

The application of microfabrication techniques, microfluidics, and microbiosensors offers an opportunity for study of the molecular mechanism of tumor angiogenesis as well as leukocyte and cancer cell extravasation. For example, the systematic examination of the role of Tie2 and VEGF in vascular formation and remodeling and may identify more specific molecular targets for anti-angiogenic therapy. A similar microdevice model could be used to examine leukocyte and cancer cell extravasation. These bioreactors will provide an appropriate cellular environment to host mouse tumor explants, thereby potentially providing a metastasis assay for tumor biopsy material. Metabolic sensing in these bioreactors will help provide a clearer understanding of the tumor microenvironment and confirm the validity of our in vitro systems[62-65].

Without intent to limit the scope of the invention, exemplary devices, application of them and related observations according to the embodiments of the present invention are given below. Note that titles or subtitles may be used in the examples for convenience of a reader, which in no way should limit the scope of the invention. Moreover, certain theories may have been proposed and disclosed herein; however, in no way they, whether they are right or wrong, should limit the scope of the invention so long as the devices and applications of them are practiced according to the invention without regard for any particular theory or scheme of action.

EXAMPLES

Bioreactor With One Barrier

Figure 1B:
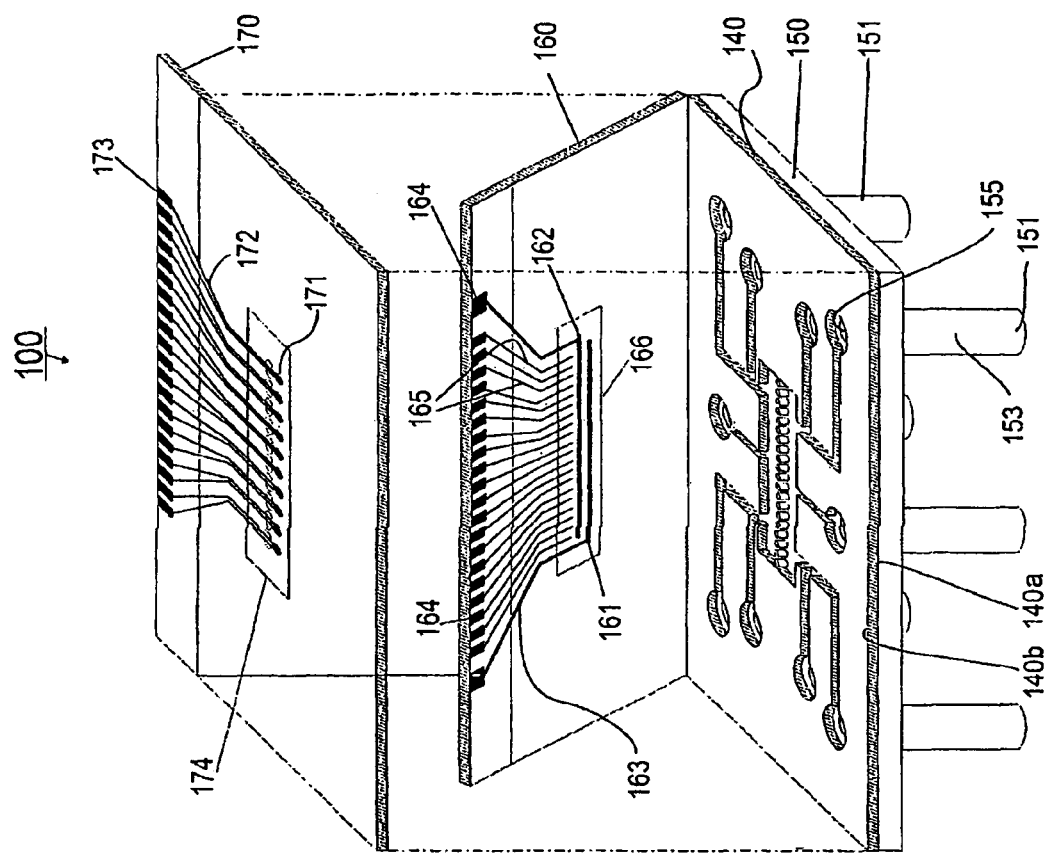
FIG. 1B shows a perspective view of a bioreactor according to another embodiment of the present invention.

Referring now to FIGS. 1A and 1B, the present invention can be practiced in association with an inventive bioreactor 100 as shown in FIGS. 1A and 1B. In one embodiment, the bioreactor 100 includes a first substrate 140 having a first surface 140a and an opposite second surface 104b, defining a chamber 101 therebetween for receiving cells and a liquid medium. The bioreactor 100 has a barrier 104 dividing the chamber 101 into a first subchamber 102 and a second subchamber 103, wherein the barrier 104 has a porosity to allow the first subchamber 102 and the second subchamber 103 in fluid communication and allow at least one predetermined type of cells to permeate between the first subchamber 102 and the second subchamber 103. The porosity of the barrier 104 can also be chosen not to let any cells to permeate.

As formed, the first subchamber 102 is adapted for receiving a first type of material such as cells 113 and the second subchamber 103 is adapted for receiving a second type of material such as cells 114, wherein each of the first type of material and the second type of material contains at least one selected from the group of cells, chemicals, and fluids. The cells can be any type of living cells, including, but not limited to, bacteria, protozoa, or both, normal cells, tumor cells, or any combination of them.

A biocompatible coating layer 116 can be applied to the chamber walls of the bioreactor 100, wherein the biocompatible coating layer 116 includes a material that may inhibit cell adhesion to the biocompatible coating layer, enhance cell adhesion to the biocompatible coating layer, or function as a fluorescent marker or indicator of the state of cells.

The bioreactor 100 further includes at least one or more inlet ports 105, 106 and one or more corresponding input transfer channel 112, 107. As formed, the input transfer channel 112 is in fluid communication with the corresponding inlet port 105 and the first subchamber 102, and the input transfer channel 107 is in fluid communication with the corresponding inlet port 106 and the second subchamber 103 for allowing delivery of the cells, fluids or chemicals to the corresponding subchamber 102 or 103, respectively. For example, a fluid can be introduced from an external device (not shown) into the first subchamber 102 through the inlet port 105 and the corresponding input transfer channel 112. Inlet ports 105, 106 each can be in fluid communication with an external device or port (not shown).

The bioreactor 100 additionally includes at least one or more outlet ports 111, 109 and one or more corresponding outlet transfer channel 110, 108. As formed, the outlet transfer channel 110 is in fluid communication with the corresponding outlet port 111 and the first subchamber 102, and the outlet transfer channel 108 is in fluid communication with the corresponding outlet port 109 and second subchamber 103 for allowing removal of the cells, fluids or chemicals from the corresponding subchamber 102 or 103, respectively. For example, a fluid can be introduced away from the first subchamber 102 through the outlet transfer channel 110 and the corresponding outlet port 111. Outlet ports 111, 109 each can be in fluid communication with an external device or port (not shown).

The bioreactor 100 further includes at least one or more auxiliary ports 115 and one or more auxiliary channels 115a. As formed, each auxiliary channel 115a is in fluid communication with a corresponding auxiliary port 115 and a corresponding one of the input transfer channels 112, 107 and the outlet transfer channels 110, 108 for flushing the corresponding transfer channel. Auxiliary ports 115 each can be in fluid communication with an external device or port (not shown). Auxiliary ports 115 and auxiliary channels 115a can be utilized to prevent clogging by cells or cellular debris in the bioreactor 100. They can also be utilized to selectively apply coatings to the channels to which they are in fluid communication.

The bioreactor 100 additionally includes one or more access ports 117 and one or more access channels 117a. As formed, each access channel 117a is in fluid communication with a corresponding access port 117 and a corresponding one of the first subchamber 102 and the second subchamber 103 for allowing delivery or removal of the cells, fluids, chemicals, coating material or sensing material to the corresponding subchamber. The access ports 117 and corresponding access channels 117a are strategically positioned so as to provide direct access to the first subchamber 102 and the second subchamber 103. For example, a fluid can be introduced into the first subchamber 102 through an access channels 117a and the corresponding access port 117 fast because the distance between the access port 117 and the first subchamber 102 is the shortest for this embodiment. Each access port 117 can be in fluid communication with an external device or port (not shown).

Moreover, the bioreactor 100 has a second substrate 150, wherein the second substrate 150 is positioned adjacent to the first surface 140a of the first substrate 140 and defines a plurality of connection channels 155. Each of the connection channels 155 is formed so as to be in fluid communication with a corresponding one of the inlet ports 105, 106, the outlet ports 111, 109, the auxiliary ports 115, and the access ports 117 as set forth above.

The bioreactor 100 further includes a plurality of connection ports 151 corresponding to the plurality of connection channels 155. Each of the connection ports 151 is formed with a channel 153 and is strategically positioned to the second substrate 150 such that each channel 153 of the connection ports 151 is in fluid communication with a corresponding one of the connection channels 155 formed in the second substrate 150 as shown in FIG. 1B.

The first substrate 140 can be fabricated from glass, Mylar, PDMS, silicon, a polymer, a semiconductor, or any combination of them. The barrier 104 is formed with a porous material. The barrier 104 can be microfabricated so as to form a structure allowing the fluid communication between the first subchamber 102 and the second subchamber 103, which may allow permeation of the barrier 104 by certain predetermined types of cells but not by other types of cells. For example, in the embodiment shown in FIGS. 1A and 1B, the barrier 104 is formed with a plurality of posts spaced from each other so as to allow bacteria to cross over but not protozoa.

The bioreactor 100 further has a third substrate 160, which is positioned adjacent to the first surface of the first substrate 140, and means strategically positioned in the third substrate 160 and adapted for electrochemical measurements of the cells responsive to the liquid medium in one or both of the first subchamber 102 and the second subchamber 103. The third substrate 160 can be formed with a semiconductor material such as silicon.

In one embodiment as shown in FIG. 1B, the means for electrochemical measurements includes a reference electrode 161, a counter electrode 162, a plurality of edge connector pads 164, and a plurality of electrically conductive leads 163. A first electrically conductive lead 163 electrically couples the reference electrode 161 to a corresponding edge connector pad 164, and a second electrically conductive lead 163 electrically couples the counter electrode 162 to a corresponding edge connector pad 164. The means for electrochemical measurements further includes a plurality of individually addressable working electrodes 165. Each of the plurality of individually addressable working electrodes 165 is electrically coupled to a corresponding edge connector pad 164 through a corresponding electrically conductive lead 163. The sensing heads of the plurality of individually addressable working electrodes 165 are strategically positioned in a region shown by outline 166 in FIG. 1B.

In operation, the liquid medium being introduced into one or both of the first subchamber 102 and the second subchamber 103 may include one or more analytes, and the plurality of individually addressable working electrodes are adapted for sensing the concentration of a single analyte of the liquid medium at multiple locations in the chamber 101 or the concentrations of a plurality of analytes of the liquid medium at multiple locations in the chamber 101 at a time period shorter than a characteristic reaction time related to at least one of cellular physiological activities of the cells. The plurality of individually addressable working electrodes can be further adapted to be capable of measuring the metabolic variables related to the cells responsive to the liquid medium at multiple locations in the chamber 101 at a time period shorter than a characteristic reaction time related to at least one of cellular physiological activities of the cells. The sensing heads of the plurality of individually addressable working electrodes 165 are strategically positioned in a region shown by outline 166 corresponding to that of the chamber 101 to perform such tasks.

The bioreactor 100 further includes a fourth substrate 170, wherein the fourth substrate 170 is positioned above the second surface 140b of the first substrate 140, and means strategically positioned in the fourth substrate 170 and adapted for optical measurements of the cells responsive to the liquid medium in at least one of the first subchamber 102 and the second subchamber 103. The fourth substrate 170 is at least partially transparent. For examples, it can be formed with a semiconductor material or a glass or both.

In one embodiment as shown in FIG. 1B, the means for optical measurements includes a plurality of optical sensors 171, a plurality of edge connector pads 173, and a plurality of leads 172, each coupling an optical sensor 171 to a corresponding edge connector pad 173. The plurality of optical sensors 171 may include at least one device selected from the group of an LED and photodiode pair, a fiber optic coupler, and an optical detecting head.

In operation, the liquid medium being introduced into one or both of the first subchamber 102 and the second subchamber 103 may include one or more analytes, and the plurality of optical sensors 171 are adapted to be capable of sensing the concentration of a single analyte of the liquid medium at multiple locations in the chamber 101 or the concentrations of a plurality of analytes of the liquid medium at multiple locations in the chamber 101 at a time period shorter than a characteristic reaction time related to at least one of cellular physiological activities of the cells. The plurality of optical sensors 171 can be further adapted for measuring the metabolic variables related to the cells responsive to the liquid medium at multiple locations in the chamber 101 at a time period shorter than the characteristic reaction time related to at least one of cellular physiological activities of the cells. The sensing heads of the plurality of optical sensors 171 are strategically positioned in a region shown by outline 174 corresponding to that of the chamber 101 to perform such tasks.

Bioreactor With Multiple Barriers

Figure 2:
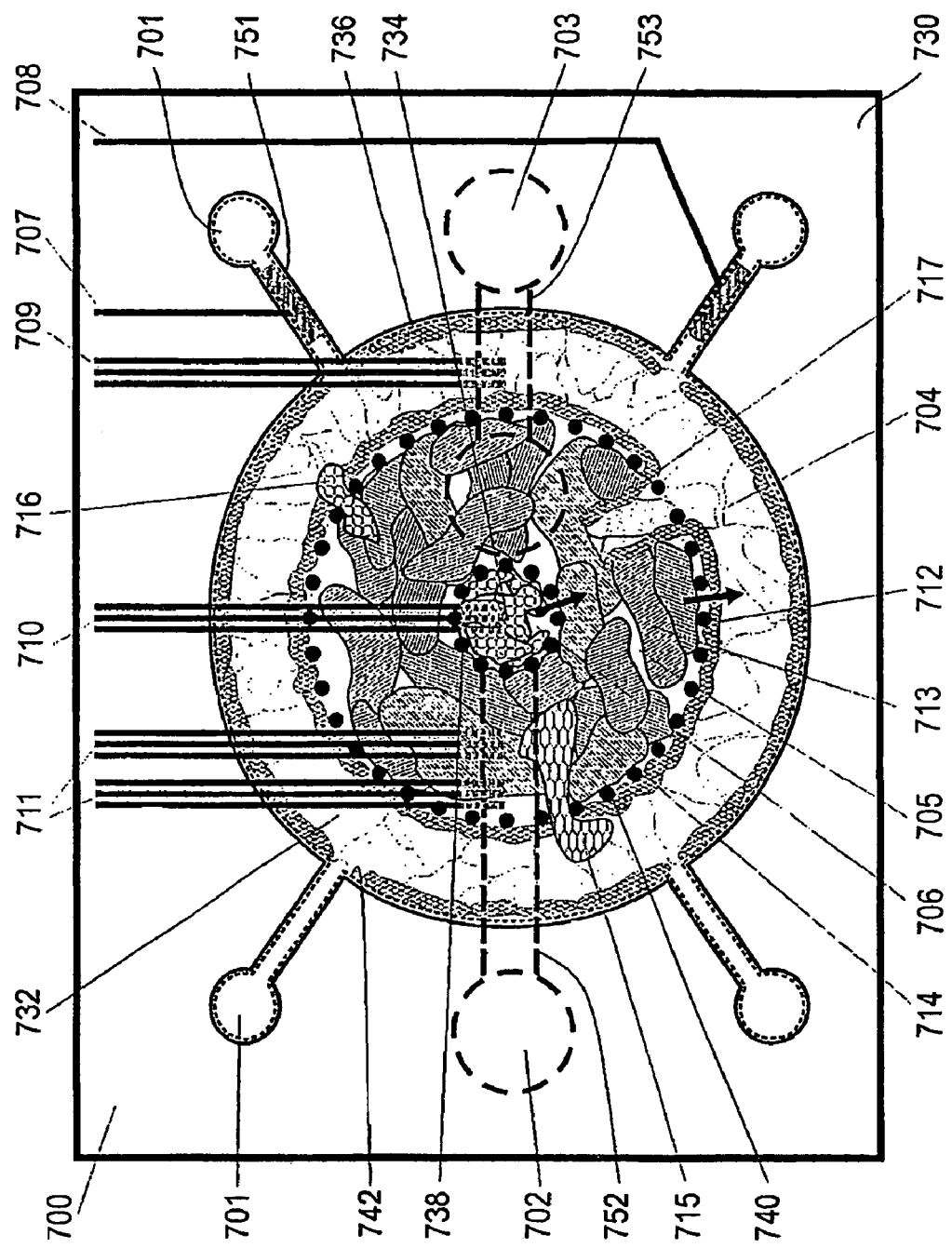
FIG. 2 schematically shows a top view of a bioreactor according to yet another embodiment of the present invention.

Referring now to FIG. 2, the present invention can also be practiced in association with an inventive bioreactor 700 as shown in FIG. 2. In one embodiment, the bioreactor 700 includes a substrate 730 having a first surface and an opposite second surface, defining a chamber 732 therebetween for receiving cells and a liquid medium, wherein the chamber 732 is formed with a center 734 and a boundary 736. The bioreactor 700 also has a first barrier 738, which encloses the center 734 and a portion of the chamber 732 to form a central chamber 706, and a second barrier 740, which is positioned between the first barrier 738 and the boundary 736 so as to form an intermediate chamber 705 and an outer chamber 704.

In one embodiment, the first barrier 738 has a first porosity to allow the central chamber 706 and the intermediate chamber 705 in fluid communication and allow at least a first predetermined type of cells to permeate between the central chamber 706 and the intermediate chamber 705, and the second barrier 740 has a second porosity to allow the outer chamber 704 and the intermediate chamber 705 in fluid communication and allow at least a second predetermined type of cells to permeate between the outer chamber 704 and the intermediate chamber 705.

Moreover, the central chamber 706 is adapted for receiving a first type of material such as tumor cells 714, the intermediate chamber 705 is adapted for receiving a second type of material such as normal tissue cells 713, and the outer chamber 704 is adapted for receiving a third type of material such as endothelial cells 712. Each of the first type of material, the second type of material and the third type of material contains at least one selected from the group of cells, chemicals, and fluids.

The first predetermined type of cells includes tumor cells 714, which normally is received in the central chamber 706 that is formed to simulate a tumor space. The second predetermined type of cells includes normal tissue cells 713, which normally is received in the intermediate chamber 705 that is formed to simulate a tissue space. Furthermore, the outer chamber 704 is formed to simulate a vascular space adapted for receiving endotlielial cells, macrophage cells, neutophil cells, any combination of them, or other immune cell type.

A biocompatible coating layer 742 can be applied to the chamber walls at the boundary 736, wherein the biocompatible coating layer 742 includes a material that may inhibit cell adhesion to the biocompatible coating layer, enhance cell adhesion to the biocompatible coating layer, or function as a fluorescent marker or indicator of the state of cells.

The bioreactor 700 further includes one or more inlet or outlet ports 701 and corresponding one or more input or output transfer channels 751, where each of the input or output transfer channel 751 is in fluid communication with a corresponding inlet or outlet port 701 and the outer chamber 704 for allowing delivery of cells, fluids or chemicals to the outer chamber 704.

The bioreactor 700 additionally may include one or more inlet or outlet ports 702 and corresponding one or more input or output transfer channels 752, where each of the input or output transfer channels 752 is in fluid communication with a corresponding inlet or outlet port 702 and the central chamber 706 for allowing delivery of the cells, fluids or chemicals to the central chamber 706.

The bioreactor 700 may further include one or more inlet or outlet ports 703 and corresponding one or more input or output transfer channels 753, where each of the input or output transfer channels 753 is in fluid communication with a corresponding inlet or outlet port 703 and the intermediate chamber 705 for allowing delivery of the cells, fluids or chemicals to the intermediate chamber 705.

The substrate 730 can be fabricated from glass, Mylar, PDMS, silicon, a polymer, a semiconductor, or any combination of them. The first barrier 738 is formed with a porous material. The first barrier 738 can be microfabricated so as to form a first structure allowing the fluid communication between the central chamber 706 and the intermediate chamber 705. The second barrier 740 is formed with a porous material. The second barrier 740 can be microfabricated so as to form a second structure allowing the fluid communication between the outer chamber 704 and the intermediate chamber 705. The first barrier 738 and the second barrier 740 can be formed with same or different porous materials. And the second structure can be same or different from the first structure. For example, in the embodiment shown in FIG. 2, the first barrier 738 is formed with a plurality of posts spaced from each other more condensed than the second barrier 740. The first barrier 738 and the second barrier 740 can also be formed into same or different shapes. For example, in the embodiment shown in FIG. 2, the first barrier 738 and the second barrier 740 are substantially circular. The boundary 736 can take various geometric shapes as well. For example, in the embodiment shown in FIG. 2, the boundary 736 is substantially circular.

The bioreactor 700 further includes means strategically positioned and adapted for electrochemical measurements of the cells responsive to the liquid medium in one or more of the outer chamber 704, the intermediate chamber 705 and the central chamber 706.

In one embodiment as shown in FIG. 2, the means for electrochemical measurements includes a reference electrode 707, a counter electrode 708, and a plurality of individually addressable working electrodes.

In operation, the liquid medium being introduced into one or more of the outer chamber 704, the intermediate chamber 705 and the central chamber 706 may include one or more analytes, and the plurality of individually addressable working electrodes include a first group of individually addressable working electrodes 709, a second group of individually addressable working electrodes 710 and a third group of individually addressable working electrodes 711, respectively.

For the embodiment shown in FIG. 2, the first group of individually addressable working electrodes 709 are adapted to be capable of sensing the concentration of a single analyte of the liquid medium at multiple locations in the outer chamber 704 or the concentrations of a plurality of analytes of the liquid medium at multiple locations in the outer chamber 704 at a time period shorter than a characteristic reaction time related to at least one of cellular physiological activities of the cells. The first group of individually addressable working electrodes 709 are further adapted to be capable of measuring the metabolic variables related to the cells responsive to the liquid medium at multiple locations in the outer chamber 704 at a time period shorter than a characteristic reaction time related to at least one of cellular physiological activities of the cells.

The second group of individually addressable working electrodes 710 adapted to be capable of sensing the concentration of a single analyte of the liquid medium at multiple locations in the central chamber 706 or the concentrations of a plurality of analytes of the liquid medium at multiple locations in the central chamber 706 at a time period shorter than a characteristic reaction time related to at least one of cellular physiological activities of the cells. The second group of individually addressable working electrodes 710 are further adapted to be capable of measuring the metabolic variables related to the cells responsive to the liquid medium at multiple locations in the central chamber 706 at a time period shorter than a characteristic reaction time related to at least one of cellular physiological activities of the cells.

Similarly, the third group of individually addressable working electrodes 711 are adapted to be capable of sensing the concentration of a single analyte of the liquid medium at multiple locations in the intermediate chamber 705 or the concentrations of a plurality of analytes of the liquid medium at multiple locations in the intermediate chamber 705 at a time period shorter than a characteristic reaction time related to at least one of cellular physiological activities of the cells. The third group of individually addressable working electrodes 711 are further adapted to be capable of measuring the metabolic variables related to the cells responsive to the liquid medium at multiple locations in the intermediate chamber 705 at a time period shorter than a characteristic reaction time related to at least one of cellular physiological activities of the cells.

As such formed, among other things, bioreactor 700 can be utilized to nurture, culture, observe, detect and explore cells, collection of cells, biofilm formed by cells and related cell activities. For examples, as shown in FIG. 2, bioreactor 700 allows a spectrum of cell activities to take place, including: a cell 715, which can be an immune type of cell such as a macrophage or neutophil, undergoing extravasation across the second barrier 740 from the outer chamber 704 into the intermediate chamber 705, a cell 716, which can be a tumor cell metastasizing from the central chamber 706 through the surrounding tissue into the vascular space, undergoing intravasation across the second barrier 740 from the intermediate chamber 705 into the outer chamber 704, and a cell 717, for example, an endothelial cell, undergoing tube formation across the second barrier 740 that may eventually lead to vascularization of the tumor, respectively.

While there has been shown various embodiments of the present invention, it is to be understood that certain changes can be made in the form and arrangement of the elements of the apparatus and steps of the methods to practice the present invention as would be known to one skilled in the art without departing from the underlying scope of the invention as is particularly set forth in the Claims. Furthermore, the embodiments described above are only intended to illustrate the principles of the present invention and are not intended to limit the claims to the disclosed elements. Indeed, since many embodiments of the invention can be made without departing from the spirit and scope of the invention, the invention resides in the claims hereinafter appended.

LIST OF REFERENCES

1. Godbey, W. T. and Atala, A., In Vitro Systems for Tissue Engineering, Ann. N.Y., Acad. Sci., 961, 10-26, 2002.
2. Murdin, A. D., Thorpe, J. S., Kirkby, N., Groves, D. J., Spier, R. E., Immobilisation and Growth of Hybridomas in Packed Beds, In: Bioreactors and biotransformations, Moody, G. W. and Baker, P. B., eds. Elsevier Applied Science Publishers, London, New York, 99-110, 1987.
3. De Bartolo, L., Jarosch-Von Schweder, G., Haverich, A., Bader, A., A Novel Full-Scale Flat Membrane Bioreactor Utilizing Porcine Hepatocytes: Cell Viability and Tissue-Specific Functions, Biotechnol. Prog., 16, 102-108, 2000.
4. McDuffie, N. G., Cell Culture Bioreactors. In: Bioreactor Design Fundamentals, Butterworth-Heinemann, Boston, 93-119, 1991.
5. Drioli, E, et al., Biocatalytic Membrane Reactors, Applications in Biotechnology and the Pharmaceutical Industry, Taylor & Francis, London, Philadelphia, 1999.
6. Labecki, M., Bowen, B. D., Piret, J. M., Protein Transport in Ultrafiltration Hollow-Fiber Bioreactors for Mammalian Cell Culture, In: Membrane Separations in Biotechnology, Wang, W. K., ed., M. Dekker, New York, 1-62, 2001.
7. Nollert, M. U., Diamond, S. L., McIntire, L. V., Hydrodynamic Shear-Stress and Mass-Transport Modulation of Endothelial-Cell Metabolism, Biotechnol. Bioeng., 38, 588-602, 1991.
8. Augenstein, D. C., Sinskey, A. J., Wang, D. I. C., Effect of Shear on Death of Two Strains of Mammalian Tissue Cells, Biotechnol. Bioeng., 13, 409-418, 1971.
9. Millward, H. R., Bellhouse, B. J., Sobey, I. J., The Vortex Wave Membrane Bioreactor: Hydrodynamics and Mass Transfer, Chemical Engineering Journal and the Biochemical Engineering Journal, 62, 175-181, 1996.
10. Beeton, S., Bellhouse, B. J., Knowles, C. J., Millward, H. R., Nicholson, A. M., Wyatt, J. R., A Novel Membrane Bioreactor for Microbial-Growth, Appl. Microbiol. Biotechnol., 40, 812-817, 1994.
11. Hu, W. S. and Aunins, J. G., Large-Scale Mammalian Cell Culture, Curr. Opin. Biotechnol., 8, 148-153, 1997.
12. Tobert, W. R., Lewis, C. Jr., White, P. J., Feder, J., Perfusion Culture Systems for Production of Mammalian Cell Biomolecules, In: Large-Scale Mammalian cell culture, Feder, J. and Tolbert, W. R., eds.; Academic Press, Orlando, 97-123, 1985.
13. Voisard, D., Meuwly, F., Ruffieux, P. A., Baer, G., Kadouri, A., Potential of Cell Retention Techniques for Large-Scale High-Density Perfusion Culture of Suspended Mammalian Cells, Biotechnol. Bioeng., 82, 751-765, 2003.
14. MacNeill, B. D., Pomerantseva, I., Lowe, H. C., Oesterle, S. N., Vacanti, J. P., Toward a New Blood Vessel, Vasc. Med., 7, 241-246, 2002.
15. Wu, H. K., Odom, T. W., Chiu, D. T., Whitesides, G. M., Fabrication of Complex Three-Dimensional Microchannel Systems in PDMS, J. Am. Chem. Soc., 125, 554-559, 2003.
16. Griffith, L. G., Emerging Design Principles in Biomaterials and Scaffolds for Tissue Engineering, Reparative Medicine: Growing Tissues and Organs, 961, 83-95, 2002.
17. Snyder, J. D. and Desai, T. A., Fabrication of Multiple Microscale Features on Polymer Surfaces for Applications in Tissue Engineering, Biomedical Microdevices, 3, 293-300, 2001.
18. Solan, A., Prabhakar, V., Niklason, L., Engineered Vessels: Importance of the Extracellular Matrix, Transplant. Proc., 33, 66-68, 2001.
19. Griffith, L. G. and Naughton, G., Tissue Engineering—Current Challenges and Expanding Opportunities, Science, 295, 1009-+, 2002.
20. Powers, M. J., Domansky, K., Kaazempur-Mofrad, M. R., Kalezi, A., Capitano, A., Upadhyaya, A., Kurzawski, P., Wack, K. E., Stolz, D. B., Kamm, R., Griffith, L. G., A Microfabricated Array Bioreactor for Perfused 3D Liver Culture, Biotechnol. Bioeng., 78, 257-269, 2002.
21. Park, T. H. and Shuler, M. L, Integration of Cell Culture and Microfabrication Technology, Biotechnol. Prog., 19, 243-253, 2003.
22. Borenstein, J. T., Terai, H., King, K. R., Weinberg, E. J., Kaazempur-Mofrad, M. R., Vacanti, J. P., Microfabrication Technology for Vascularized Tissue Engineering, Biomedical Microdevices, 4, 167-175, 2002.
23. Kaihara, S., Borenstein, J., Koka, R., Lalan, S., Ochoa, E. R., Ravens, M., Pien, H., Cunningham, B., Vacanti, J. P., Silicon Micromachining to Tissue Engineer Branched Vascular Channels for Liver Fabrication, Tissue Eng., 6, 105-117, 2000.
24. Allen, J. W. and Bhatia, S. N., Improving the Next Generation of Bioartificial Liver Devices, Seminars in Cell & Developmental Biology, 13, 447-454, 2002.
25. Passeraub, P. A., Almeida, A. C., Thakor, N. V., Design, Microfabrication and Analysis of a Microfluidic Chamber for the Perfusion of Brain Tissue Slices, Biomedical Microdevices, 5, 147-155, 2003.
26. Fink, C., Ergun, S., Kralisch, D., Remmers, U., Weil, J., Eschenhagen, T., Chronic Stretch of Engineered Heart Tissue Induces Hypertrophy and Functional Improvement, FASEB J., 14, 669-679, 2000.
27. Mooney, D. T., Mazzoni, C. L., Breuer, C., McNamara, K., Hern, D., Vacanti, J. P., Langer, R., Stabilized Polyglycolic Acid Fibre Based Tubes for Tissue Engineering, Biomaterials, 17, 115-124, 1996.
28. Boyden, S., The Chemotactic Effect of Mixtures of Antibody and Antigen on Polymorphonuclear Leucocytes, J. Exp. Med., 115, 453-466, 1962.
29. Harvath, L., Falk, W., Leonard, E. J., Rapid Quantitation of Neutrophil Chemotaxis—Use of A Polyvinylpyrrolidone-Free Polycarbonate Membrane in A Multiwell Assembly, J. Immunol. Methods, 37, 39-45, 1980.
30. Falk, W., Goodwin, R. H., Leonard, E. J., A 48-Well Micro Chemotaxis Assembly for Rapid and Accurate Measurement of Leukocyte Migration, J. Immunol. Methods, 33, 239-247, 1980.
31. Yao, J., Harvath, L., Gilbert, D. L., Colton, C. A., Chemotaxis by A Cns Macrophage, the Microglia, J. Neurosci. Res., 27, 36-42, 1990.
32. Roth, S. J., Carr, M. W., Rose, S. S., Springer, T. A., Characterization of Transendothelial Chemotaxis of T Lymphocytes, J. Immunol. Methods, 188, 97-116, 1995.
33. Klemke, R. L., Leng, J., Molander, R., Brooks, P. C., Vuori, K., Cheresh, D. A., CAS/Crk Coupling Serves As a "Molecular Switch" for Induction of Cell Migration, Journal of Cell Biology, 140, 961-972, 1998.
34. Ding, Z., Xiong, K., Issekutz, T. B., Chemokines Stimulate Human T Lymphocyte Transendothelial Migration to Utilize VLA-4 in Addition to LFA-1, J. Leukoc. Biol., 69, 458-466, 2001.
35. Jones, D. A., Abbassi, O., McIntire, L. V., McEver, R. P., Smith, C. W., P-Selectin Mediates Neutrophil Rolling on Histamine-Stimulated Endothelial Cells, Biophys. J., 65, 1560-1569, 1993.
36. Brown, D. and Larson, R., Improvements to Parallel Plate Flow Chambers to Reduce Reagent and Cellular Requirements, BMC Immunology, 2, 9-16, 2001.
37. Cinamon, G. and Alon, R., A Real Time in Vitro Assay for Studying Leukocyte Transendothelial Migration Under Physiological Flow Conditions, J. Immunol. Methods, 273, 53-62, 2003.
38. Renard, M., Heutte, F., Boutherin-Falson, O., Finet, M., Boisseau, M. R., Induced Changes of Leukocyte Slow Rolling in an in Flow Pharmacological Model of Adhesion to Endothelial Cells, Biorheology, 40, 173-178, 2003.
39. Munn, L. L., Melder, R. J., Jain, R. K., Analysis of Cell Flux in the Parallel-Plate Flow Chamber—Implications for Cell Capture Studies, Biophys. J., 67, 889-895, 1994.
40. Ley, K., The Selectins As Rolling Receptors. In: The selecting: initiators of leukocyte endothelial adhesion, Vestweber, D, ed. Harwood Academic Publishers, Australia, 63-104, 1997.
41. Papadaki, M. and McIntire, L. V., Quantitative Measurement of Shear-Stress Effects on Endothelial Cells. In: Tissue engineering methods and protocols, Morgan, J. R. and Yarmush, M. L, eds. Humana Press, Totowa, N.J., 577-593, 1999.
42. Ramos, C. L. and Lawrence, M. B., Quantitative Measurement of Cell-Cell Adhesion Under Flow Conditions, In: Tissue engineering methods and protocols, Morgan, J. R. and Yarmush, M. L., eds. Humana Press, Totowa, N.J., 507-519, 1999.
43. Hammer, D. A. and Brunk, D. K., Measuring Receptor-Mediated Cell Adhesion Under Flow: Cell-Free Systems. In: Tissue engineering methods and protocols, Morgan, J. R. and Yarmush, M. L., eds; Humana Press, Totowa, N.J., 543-552, 1999.
44. Jain, R. K., Munn, L. L., Fukumura, D., Melder, R. J., In Vitro and In Vivo Quantification of Adhesion Between Leukocytes and Vascular Endothelium. In: Tissue engineering methods and protocols, Morgan, J. R. and Yarmush, M. L., eds. Humana Press, Totowa, N.J., 553-575, 1999.
45. Li, C. Y., Shan, S., Huang, Q., Braun, R. D., Lanzen, J., Hu, K., Lin, P., Dewhirst, M. W., Initial Stages of Tumor Cell-Induced Angiogenesis: Evaluation Via Skin Window Chambers in Rodent Models, J Natl Cancer Inst, 92, 143-7, 2000.
46. Jain, R. K., Munn, L. L., Fukumura, D., Dissecting Tumour Pathophysiology Using Intravital Microscopy. Nat Rev Cancer, 2, 266-76, 2002.
47. Jain, R. K., Munn, L. L., Fukumura, D., Dissecting Tumour Pathophysiology Using Intravital Microscopy. Nature Reviews Cancer, 2, 266-276, 2002.
48. Jain, R. K., Angiogenesis and Lymphangiogenesis in Tumors: Insights From Intravital Microscopy, Cold Spring Harb. Symp. Quant. Biol., 67, 239-248, 2002.
49. Folkman, J., Bach, M., Rowe, J. W., Davidoff, F., Lambert, P., Hirsch, C., Goldberg, A., Hiatt, H. H., Glass, J., Henshaw, E., Tumor Angiogenesis—Therapeutic Implications, N. Engl. J. Med., 285, 1182-1186, 1971.
50. Weidner, N., Semple, J. P., Welch, W. R., Folkman, J., Tumor Angiogenesis and Metastasis—Correlation in Invasive Breast-Carcinoma, N. Engl. J. Med., 324, 1-8, 1991.
51. Lin, P., Buxton, J. A., Acheson, A, Radziejewski, C, Maisonpierre, P. C., Yancopoulos, G. D., Channon, K. M., Hale, L. P., Dewhirst, M. W., George, S. E., Peters, K. G., Antiangiogenic Gene Therapy Targeting the Endothelium-Specific Receptor Tyrosine Kinase Tie2, Proc. Natl Acad Sci USA 95, 8829-34, 1998.
52. Lin, P., Polverini, P., Dewhirst, M., Shan, S., Rao, P. S., Peters, K., Inhibition of Tumor Angiogenesis Using a Soluble Receptor Establishes a Role for Tie2, in Pathologic Vascular Growth, J Clin Invest, 100, 2072-8, 1997.
53. Lin, P., Sankar, S., Shan, S., Dewhirst, M. W., Polverini, P. J., Quinn, T. Q., Peters, K. G., Inhibition of Tumor Growth by Targeting Tumor Endothelium Using a Soluble Vascular Endothelial Growth Factor Receptor, Cell Growth Differ, 9, 49-58, 1998.
54. Heidemann, J., Ogawa, H., Dwinell, M. B., Rafiee, P., Maaser, C., Gockel, H. R., Otterson, M. F., Ota, D. M., Lugering, N., Domschke, W., Binion, D. G., Angiogenic Effects of Interleukin 8 (CXCL8) in Human Intestinal Microvascular Endothelial Cells Are Mediated by CXCR2, J. Biol. Chem., 278, 8508-8515, 2003.
55. Li, Y., Tondravi, M., Liu, J., Smith, E., Haudenschild, C. C., Kaczmarek, M., Zhan, X., Cortactin Potentiates Bone Metastasis of Breast Cancer Cells, Cancer Res, 61, 6906-11, 2001.
56. Higgs, H. N. and Pollard, T. D., Regulation of Actin Filament Network Formation Through Arp2/3 Complex: Activation by a Diverse Array of Proteins, Annu. Rev. Biochem., 70, 649-676, 2001.
57. Li, F. Y., Zhang, L., Metzger, R. M., On the Growth of Highly Ordered Pores in Anodized Aluminum Oxide, Chem. Mater., 10, 2470-2480, 1998.
58. Li, A. P., Muller, F., Birner, A., Nielsch, K., Gosele, U., Hexagonal Pore Arrays With a 50-420 Nm Interpore Distance Formed by Self-Organization in Anodic Alumina, J. Appl. Phys., 84, 6023-6026, 1998.
59. Black, C. T., Guarini, K. W., Milkove, K. R., Baker, S. M., Russell, T. P., Tuominen, M. T., Integration of Self-Assembled Diblock Copolymers for Semiconductor Capacitor Fabrication, Appl. Phys. Lett., 79, 409-411, 2001.
60. Black; C. T. and Guarini, K. W., Diblock Copolymers: Self-Assembly for Applications in Microelectronics, In: Encyclopedia of Materials: Science and Technology, Buschow, K H J, ed. Elsevier, N.Y., 1-6, 2002.
61. Guarini, K. W., Black, C. T., Zhang, Y., Kim, H., Sikorski, E. M., Babich, I. V., Process Integration of Self-Assembled Polymer Templates into Silicon Nanofabrication, Journal of Vacuum Science & Technology B, 20, 2788-2792, 2002.
62. MartinezZaguilan, R., Seftor, E. A., Seftor, R. E. B., Chu, Y. W., Gillies, R. J., Hendrix, M. J. C., Acidic PH Enhances the Invasive Behavior of Human Melanoma Cells, Clinical & Experimental Metastasis, 14, 176-186, 1996.
63. Gillies, R. J., Raghunand, N., Karczmar, G. S., Bhujwalla, Z. M., MRI of the Tumor Microenvironment, J. Magn. Reson. Imaging, 16, 430-450, 2002.
64. Bhujwalla, Z. M., Artemov, D., Ballesteros, P., Cerdan, S., Gillies, R. J., Solaiyappan, M, Combined Vascular and Extracellular PH Imaging of Solid Tumors, NMR Biomed., 15, 114-119, 2002.
65. Helmlinger, G., Schell, A., Dellian, M., Forbes, N. S., Jain, R. K., Acid Production in Glycolysis-Impaired Tumors Provides New Insights into Tumor Metabolism, Clin. Cancer Res., 8, 1284-1291, 2002.

What is claimed is:

1. A bioreactor for cultivating living cells in a liquid medium comprising:
   (a) a first substrate having a first surface and an opposite second surface, defining a chamber therebetween for receiving and culturing the cells and receiving the liquid medium;
   (b) a barrier dividing the chamber into a first subchamber and a second subchamber, wherein the barrier comprises a porous material and has a porosity to allow the first subchamber and the second subchamber to be in fluid communication and allow at least one predetermined type of cells to permeate between the first subchamber and the second subchamber;
   (c) a second substrate positioned adjacent to the first surface of the first substrate;
   (d) a third substrate, wherein the third substrate is positioned adjacent to the second surface of the first substrate;
   (e) an electrochemical measuring system positioned in the third substrate and adapted for electrochemical measurements of the cells responsive to the liquid medium in at least one of the first subchamber and the second subchamber;
   (f) a fourth substrate positioned above the third substrate such that the third substrate forms an intermediate layer between the first substrate and the fourth substrate; and
   (g) means positioned in the fourth substrate and adapted for optical measurements of the cells responsive to the liquid medium in at least one of the first subchamber and the second subchamber.

2. The bioreactor of claim 1, wherein the first subchamber is adapted for receiving a first type of material and the second subchamber is adapted for receiving a second type of material.

3. The bioreactor of claim 2, wherein each of the first type of material and the second type of material contains at least one selected from the group of cells, chemicals, and fluids.

4. The bioreactor of claim 3, wherein the cells comprise bacteria.

5. The bioreactor of claim 3, wherein the cells comprise protozoa.

6. The bioreactor of claim 1, further comprising a biocompatible coating layer applied to the chamber walls.

7. The bioreactor of claim 6, wherein the biocompatible coating layer comprises a material that may inhibit cell adhesion to the biocompatible coating layer, enhance cell adhesion to the biocompatible coating layer, or function as a fluorescent marker or indicator of the state of cells.

8. The bioreactor of claim 1, further comprising at least one inlet port and an input transfer channel in fluid communication with the inlet port and one of the first subchamber and the second subchamber for allowing delivery of the cells, fluids or chemicals to the corresponding subchamber.

9. The bioreactor of claim 8, further comprising at least one outlet port and an outlet transfer channel in fluid communication with the outlet port and one of the first subchamber and the second subchamber for allowing removal of the cells, fluids or chemicals from the corresponding subchamber.

10. The bioreactor of claim 9, further comprising at least one auxiliary port and an auxiliary channel in fluid communication with the auxiliary port and one of the input transfer channel and the outlet transfer channel for flushing the corresponding transfer channel.

11. The bioreactor of claim 10, further comprising at least one access port and an access channel in fluid communication with the access port and one of the first subchamber and the second subchamber for allowing delivery or removal of the cells, fluids, chemicals, coating material or sensing material to the corresponding subchamber.

12. The bioreactor of claim 11, wherein the second substrate defines a plurality of connection channels, each of the connection channels being formed so as to be in fluid communication with a corresponding one of the inlet port, the outlet port, the auxiliary port, and the access port.

13. The bioreactor of claim 12, further comprising a plurality of connection ports, each of the connection ports being formed with a channel and being positioned to the second substrate such that each channel of the connection ports is in fluid communication with a corresponding one of the connection channels formed in the second substrate.

14. The bioreactor of claim 1, wherein the first substrate is fabricated from glass, Mylar, PDMS, silicon, a polymer, a semiconductor, or any combination of them.

15. The bioreactor of claim 1, wherein the barrier is microfabricated so as to form a structure allowing the fluid communication between the first subchamber and the second subchamber.

16. The bioreactor of claim 1, wherein the means for electrochemical measurements comprises:
   (i) a reference electrode;
   (ii) a counter electrode;
   (iii) a plurality of edge connector pads; and
   (iv) a plurality of electrically conductive leads, where a first electrically conductive lead electrically couples the reference electrode to a corresponding edge connector pad, and a second electrically conductive lead electrically couples the counter electrode to a corresponding edge connector pad.

17. The bioreactor of claim 16, wherein the means for electrochemical measurements further comprises:
   a plurality of individually addressable working electrodes, each being electrically coupled to a corresponding edge connector pad through a corresponding electrically conductive lead.

18. The bioreactor of claim 17, wherein the liquid medium comprises at least one analyte, and wherein the plurality of individually addressable working electrodes are adapted for sensing the concentration of a single analyte of the liquid medium at multiple locations in the chamber or the concentrations of a plurality of analytes of the liquid medium at multiple locations in the chamber at a time period shorter than a characterization reaction time related to at least one of cellular physiological activities of the cells.

19. The bioreactor of claim 18, wherein the plurality of individually addressable working electrodes are further adapted for measuring the metabolic variables related to the cells responsive to the liquid medium at multiple locations in the chamber at a time period shorter than a characterization reaction time related to at least one of cellular physiological activities of the cells.

20. The bioreactor of claim 1, wherein the third substrate comprises a semiconductor material.

21. The bioreactor of claim 20, wherein the semiconductor material comprises silicon.

22. The bioreactor of claim 1, wherein the means for optical measurements comprises:
   (i) a plurality of optical sensors;
   (ii) a plurality of edge connector pads; and
   (iii) a plurality of optically conductive leads, each optically coupling an optical sensor to a corresponding edge connector pad.

23. The bioreactor of claim 22, wherein the plurality of optical sensors comprises at least one device selected from the group of an LED and photodiode pair, a fiber optic coupler, and an optical detecting head.

24. The bioreactor of claim 23, wherein the liquid medium comprises at least one analyte, and wherein the plurality of optical sensors are adapted for sensing the concentration of a single analyte of the liquid medium at multiple locations in the chamber or the concentrations of a plurality of analytes of the liquid medium at multiple locations in the chamber at a time period shorter than a characterization reaction time related to at least one of cellular physiological activities of the cells.

25. The bioreactor of claim 24, wherein the plurality of optical sensors are further adapted for measuring the metabolic variables related to the cells responsive to the liquid medium at multiple locations in the chamber at a time period shorter than the characterization reaction time related to at least one of cellular physiological activities of the cells.

26. The bioreactor of claim 1, wherein the fourth substrate comprises a semiconductor material.

27. The bioreactor of claim 26, wherein the fourth substrate is at least partially transparent.

* * * * *